US012586482B1

(12) United States Patent
Thomure et al.

(10) Patent No.: US 12,586,482 B1
(45) Date of Patent: Mar. 24, 2026

(54) ELECTRONIC LEARNING SYSTEM

(71) Applicant: Zayed University, Dubai (AE)

(72) Inventors: Hanada Taha Thomure, Abu Dhabi (AE); Haitham Taha, Abu Dhabi (AE)

(73) Assignee: Zayed University, Dubai (AE)

( * ) Notice: Subject to any disclaimer, the term of this patent is extended or adjusted under 35 U.S.C. 154(b) by 0 days.

(21) Appl. No.: 19/031,724

(22) Filed: Jan. 18, 2025

(51) Int. Cl.
G09B 7/02 (2006.01)
G16H 50/20 (2018.01)

(52) U.S. Cl.
CPC .............. G09B 7/02 (2013.01); G16H 50/20 (2018.01)

(58) Field of Classification Search
CPC ........................................................ G09B 7/02
See application file for complete search history.

(56) References Cited

PUBLICATIONS

ArabiSARD, Web Archive, Apr. 13, 2023. < https://web.archive.org/web/20230413203038/https://www.arabisard.com:558/site> (Year: 2023).*

* cited by examiner

*Primary Examiner* — Thomas J Hong

(57) ABSTRACT

A method includes receiving, by an electronic communications system, an electronic assessment of a user, wherein the electronic communications system includes memory and a processor. The method includes receiving, by the electronic communications system, historical electronic information. The method includes analyzing by the electronic communications system the electronic assessment based on the historical information. The method includes determining, by the electronic system, a learning disability of the user.

12 Claims, 54 Drawing Sheets

Grade 1 Benchmark Score and Speed

Speed 200.0000
180.0000
160.0000
140.0000
120.0000
100.0000
80.0000
60.0000
40.0000
20.0000

8.0000
7.0000
6.0000
5.0000
4.0000
3.0000
2.0000
1.0000

Score

Task 1 Task 2 Task 3 Task 4 Task 5 Task 6 Task 7 Task 8 Task 9 Task 10 Task 11 Task 12 Task 13 Task 14

Score ——Speed

| Task | Items 1 | Items 2 |
|---|---|---|
| READING LETTERS IN THE BEGINNING, MIDDLE AND END OF WORDS | 36 | 20 |
| READING SYLLABLES | 28 | 20 |
| READING REAL WORDS | 28 | 20 |
| READING REAL WORDS WITH TASHKEEL | 30 | 20 |
| READING PSEUDOWORDS | 25 | 10 |
| PHONOLOGICAL AWARENESS | 15 | 10 |
| LETTER NAMING | 10 | 5 |
| NUMBER NAMING | 10 | 5 |
| OBJECT NAMING | 9 | 5 |

FIG. 26

| Task | READING LETTERS IN THE BEGINNING, MIDDLE AND END OF WORDS |
|---|---|
| Content 1 | (Arabic text) |
| Content 2 | (Arabic text) |

| Task | READING REAL WORDS WITH TASHKEEL |
|---|---|
| Content 1 | بَيْت – دَرْس – الْبَوّاب – قَلَم – مَاء – حَرَس – كَبير – يَأْكُل – بَاع – كَلَام – هَوَاء – رَايَة – لَوْح – هَاتِف – صَارَة – صَابُون – طَبِيب – مَنْدِيل – مُفْتَاح – قَرِيب – نَار – وَنَّ – شَاعِر – جِدَال – مُكَسَّر – قِرَاءَة – اسْتَخْدَم – النَّقْد |
| Content 2 | بَيْت – دَرْس – الْبَوّاب – قَلَم – مَاء – حَرَس – كَبير – يَأْكُل – كَلَام – نَار – وَنَّ – شَاعِر – طَبِيب – صَابُون – هَاتِف – لَوْح – هَوَاء – رَايَة – يَأْكُل – كَبير – حَرَس – مَاء – قَلَم – الْبَوّاب – دَرْس – مُكَسَّر – قِرَاءَة |

FIG. 30

READING PSEUDOWORDS

Task

Content 1

Content 2

Figure 34:
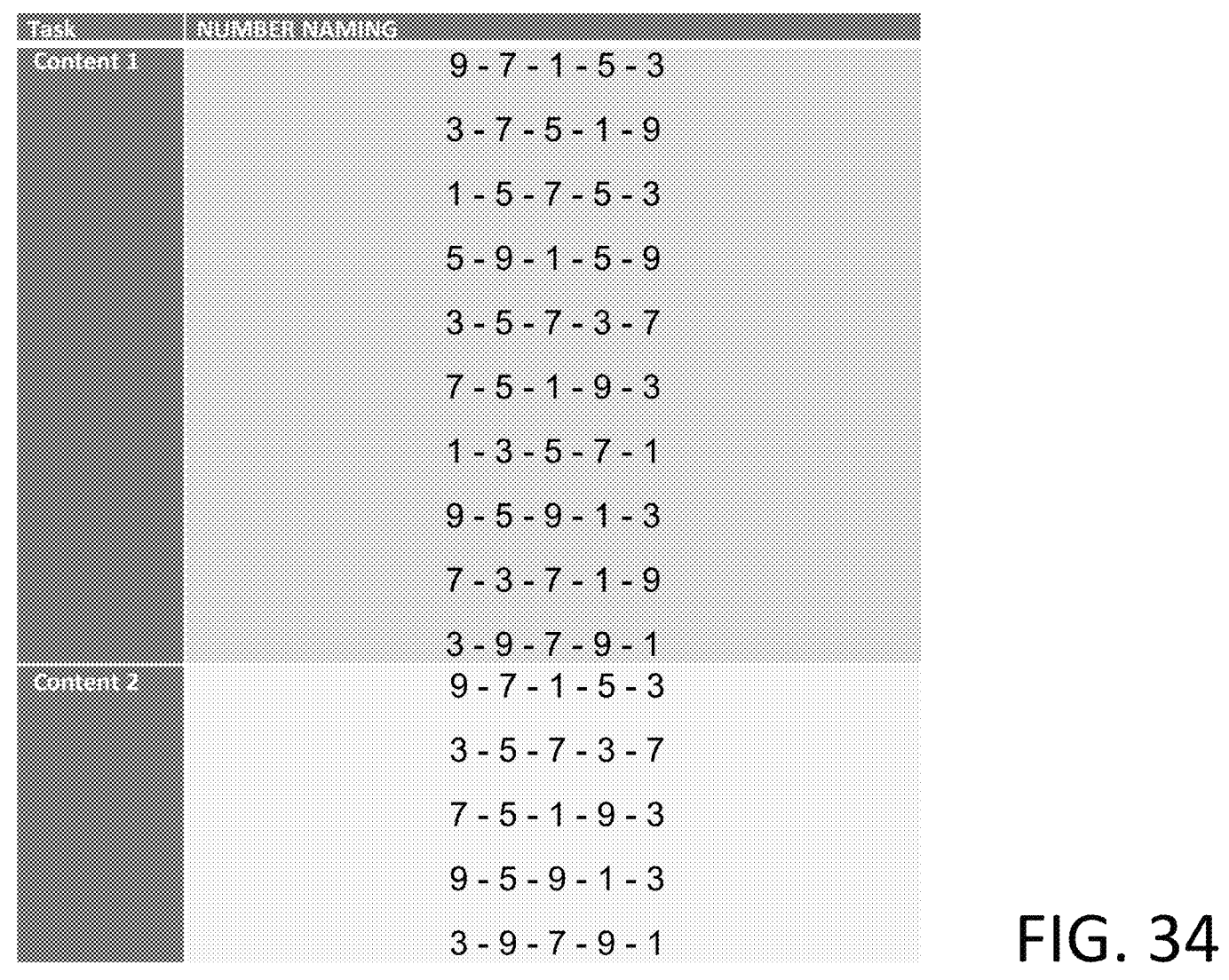

Test

NUMBER NAMING

Content 1

9 - 7 - 1 - 5 - 3
3 - 7 - 5 - 1 - 9
1 - 5 - 7 - 5 - 3
5 - 9 - 1 - 5 - 9
3 - 5 - 7 - 3 - 7
7 - 5 - 1 - 9 - 3
1 - 3 - 5 - 7 - 1
9 - 5 - 9 - 1 - 3
7 - 3 - 7 - 1 - 9
3 - 9 - 7 - 9 - 1

Content 2

Task
Content 1
Content 2
OBJECT NAMING

| Task | Question Count 1 | Question Count 2 |
|---|---|---|
| READING LETTERS IN THE BEGINNING, MIDDLE AND END OF WORDS | 36 | 20 |
| READING SYLLABLES | 28 | 20 |
| READING REAL WORDS | 28 | 20 |
| READING REAL WORDS WITH TASHKEEL | 30 | 20 |
| READING PSEUDOWORDS | 25 | 20 |
| PHONOLOGICAL AWARENESS | 15 | 10 |
| LETTER NAMING | 10 | 5 |
| NUMBER NAMING | 10 | 5 |
| OBJECT NAMING | 9 | 5 |
| ORTHOGRAPHIC DECISION | 23 | 15 |

READING SYLLABLES

Task

Content 1

Content 2

| Task | READING REAL WORDS WITH TASHKEEL |
|---|---|
| Content 1 | الثَّقَة - قَرِيب - فِلَاح - هَوَاء - تِلْوِيح - هَاتِف - صَنَابِير - صَنَبُون - مَطَر - صَنَابِير - مُشْطَى - خَائِف - نَار - حَرِس - جِدَال - مُكَبِّر - قَرَأَتْ - اسْتَخْدِم - مَكْتَبِي - دُرُوس - كَبِير - نَأْكُل - نَأْكُل - كِتَاب |
| Content 2 | مُكَبِّر - دُرُوس - حَرِس - كَبِير - نَأْكُل - نَأْكُل - مُشْطَى - خَائِف - نَار - قَرَأَتْ - اسْتَخْدِم - قَرِيب - فِلَاح - هَوَاء - تِلْوِيح - هَاتِف - صَنَابِير - مَطَر |

| Test | NUMBER NAMING |
|---|---|
| Content 1 | 9 - 7 - 1 - 5 - 3 |
| | 3 - 7 - 5 - 1 - 9 |
| | 1 - 5 - 7 - 5 - 3 |
| | 5 - 9 - 1 - 5 - 9 |
| | 3 - 5 - 7 - 3 - 7 |
| | 7 - 5 - 1 - 9 - 3 |
| | 1 - 3 - 5 - 7 - 1 |
| | 9 - 5 - 9 - 1 - 3 |
| | 7 - 3 - 7 - 1 - 9 |
| | 3 - 9 - 7 - 9 - 1 |
| Content 2 | 9 - 7 - 1 - 5 - 3 |
| | 3 - 7 - 5 - 1 - 9 |
| | 1 - 5 - 7 - 5 - 3 |
| | 5 - 9 - 1 - 5 - 9 |
| | 7 - 5 - 1 - 9 - 3 |

ORTHOGRAPHIC DECISION

Task

Content 2

| Task | Timespan 1 | Timespan 2 |
|---|---|---|
| READING LETTERS | 2 sec | 2.5 sec |
| READING LETTERS IN THE BEGINNING, MIDDLE AND OF WORDS | 2 sec | 2.5 sec |
| READING SYLLABLES | 2 sec | 2.5 sec |
| READING REAL WORDS | 2 sec | 3 sec |
| READING REAL WORDS WITH TASHKEEL | 2 sec | 3 sec |
| READING PSEUDOWORDS | 2 sec | 3 sec |
| PHONOLOGICAL AWARENESS | 10 sec | 15 sec |
| OBJECT NAMING | 5 sec | 10 sec |
| IMMEDIATE SHORT-TERM MEMORY | 3 sec | 7 sec |
| PHONOLOGICAL WORKING MEMORY | 3 sec | 7 sec |

| TEST | FACTORS |
|---|---|
| READING LETTERS | Letter Shape – Speed - Spelling |
| READING LETTERS IN THE BEGINNING, MIDDLE AND END OF WORDS | Letter Shape – Speed - Spelling |
| READING SYLLABLES | Syllables Shape – Speed – Spelling |
| READING REAL WORDS | Word Shape – Speed - Spelling |
| READING REAL WORDS WITH TASHKEEL | Word Shape – Speed – Spelling - Diacritics |
| READING PSEUDO WORDS | Word Shape – Speed – Spelling - Diacritics |
| READING TEXT | Sentence Reading – Speed - Diacritics |
| PHONOLOGICAL AWARENESS | Phonology – Speed – Visual Decision |
| LETTER NAMING | Multi Letter Image – Speed – Spelling |
| NUMBER NAMING | Multi Number Image – Speed – Spelling |
| OBJECT NAMING | Multi Object Image – Speed – Spelling |
| LISTENING COMPREHENSION | Phonology – Speed – Memory – Understanding |
| READING COMPREHENSION | Reading - Speed – Memory - Understanding |
| IMMEDIATE SHORT TERM MEMORY | Numbers - Speed – Short Term Memory |
| PHONOLOGICAL WORKING MEMORY | Numbers - Speed – Working Memory |
| ORTHOGRAPHIC DECISION | Phonology - Orthographic – Speed |

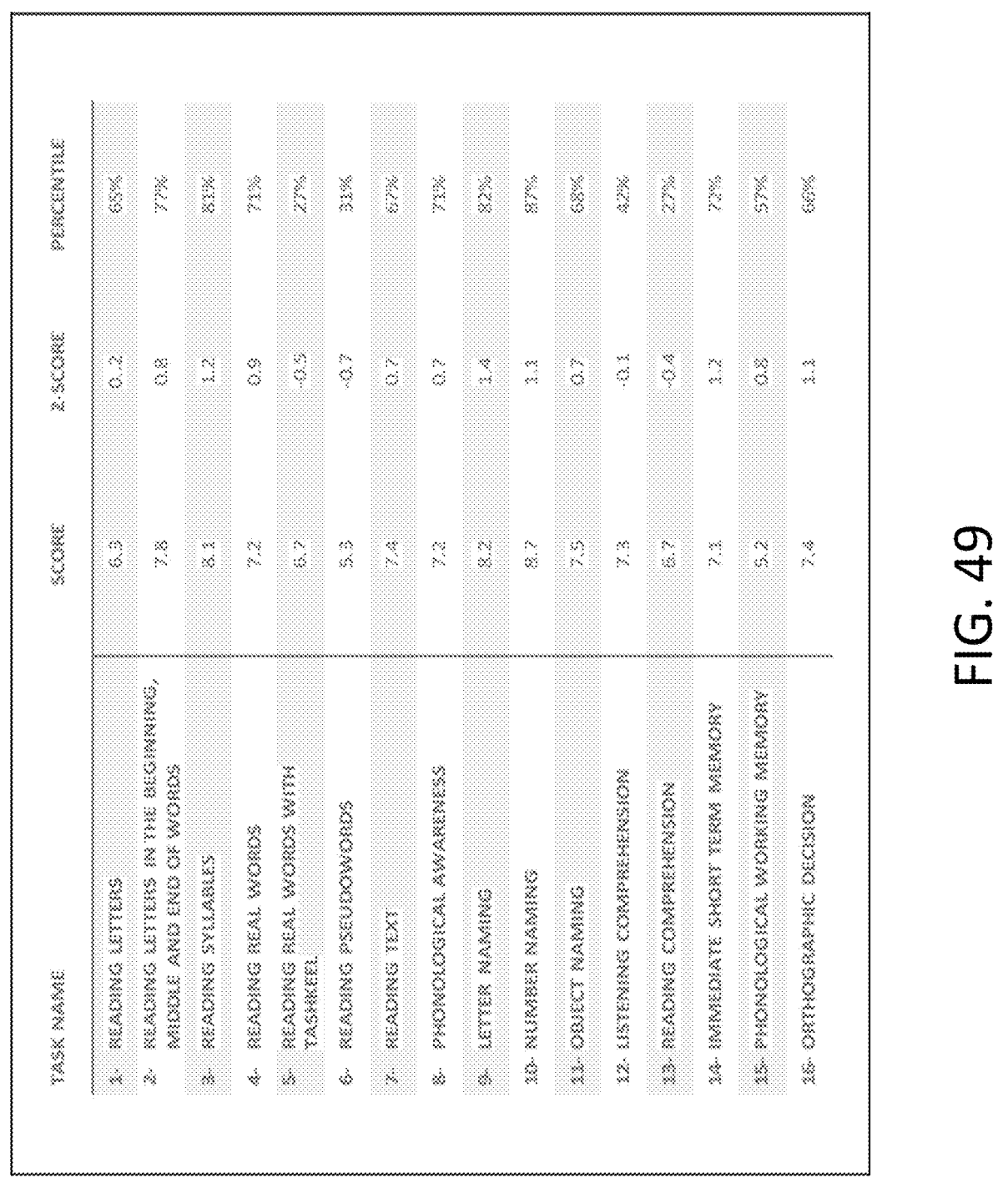

| TASK NAME | SCORE | Z-SCORE | PERCENTILE |
|---|---|---|---|
| 1. READING LETTERS | 6.9 | 0.2 | 65% |
| 2. READING LETTERS IN THE BEGINNING, MIDDLE AND END OF WORDS | 7.8 | 0.8 | 77% |
| 3. READING SYLLABLES | 8.1 | 1.2 | 85% |
| 4. READING REAL WORDS | 7.2 | 0.9 | 79% |
| 5. READING REAL WORDS WITH TASKKER. | 6.7 | -0.5 | 27% |
| 6. READING PSEUDOWORDS | 5.3 | -0.7 | 31% |
| 7. READING TEXT | 7.4 | 0.7 | 67% |
| 8. PHONOLOGICAL AWARENESS | 7.3 | 0.7 | 73% |
| 9. LETTER NAMING | 8.2 | 1.4 | 82% |
| 10. NUMBER NAMING | 8.7 | 1.1 | 87% |
| 11. OBJECT NAMING | 7.5 | 0.7 | 68% |
| 12. LISTENING COMPREHENSION | 7.3 | -0.1 | 42% |
| 13. READING COMPREHENSION | 6.7 | -0.4 | 27% |
| 14. IMMEDIATE SHORT TERM MEMORY | 7.1 | 1.2 | 72% |
| 15. PHONOLOGICAL WORKING MEMORY | 5.2 | 0.8 | 57% |
| 16. ORTHOGRAPHIC DECISION | 7.4 | 1.1 | 66% |

FIG. 49

ASSESSMENT SCALES

Assessment results for accuracy and correctness are reported on a 1 to 10 scale, with 10 being the more favourable end of the scale.

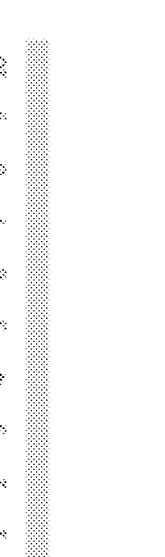

ASSESSMENT RESULTS

Scale bars are used to illustrate assessment results for accuracy and correctness.

Score:7.2

SPEED

Average, minimum, maximum and total response time per seconds are reported.

| Avg | Min | MAX |
|---|---|---|
|  |  |  |

BENCHMARKS

Bar charts are used to illustrate assessment results for accuracy / correctness, speed and memory compared to norms in same age and grade in your country (local norms) and other countries (global norms).

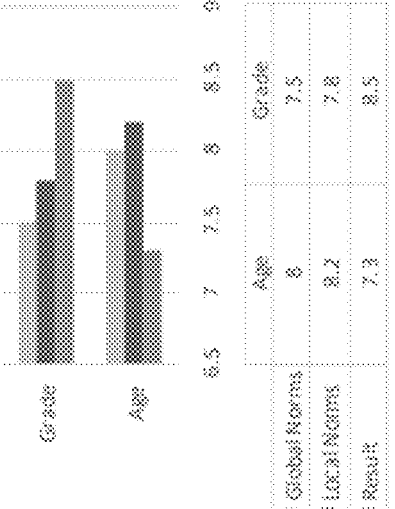

|  | Age | Grade |
|---|---|---|
| Global Norms | 8 | 7.5 |
| Local Norms | 8.2 | 7.8 |
| Result | 7.3 | 8.5 |

Global Norms   Local Norms   Result

FIG. 50

ELECTRONIC LEARNING SYSTEM

BACKGROUND

Educational tools are used by schools to assist in determining how well a student is learning. Traditional tools, such as exams and homework, provide a teacher with an understanding of how well a student progressing in a particular course. However, traditional educational tools have shortcomings. For example, many educational tools are not affective in helping students that have different learning difficulties. Also, many educational tools are not affective in teaching subject matter for students in a remote sending which is even more of a challenge when it comes to learning for young children. Furthermore, existing educational tools cannot detect if a child has any learning disabilities based on an online assessment in real-time. Although there are multiple datasets available that contain Arabic recordings of children, they are region-specific and focus on general reading rather than on reading difficulties. Accordingly, there is currently an absence of a dataset that addresses reading difficulties.

BRIEF DESCRIPTION OF DRAWINGS

FIGS. 26-48 are diagrams of example tables;
FIGS. 49 and 50 are diagrams of example graphical displays.

DETAILED DESCRIPTION OF PREFERRED EMBODIMENTS

Figure 1:
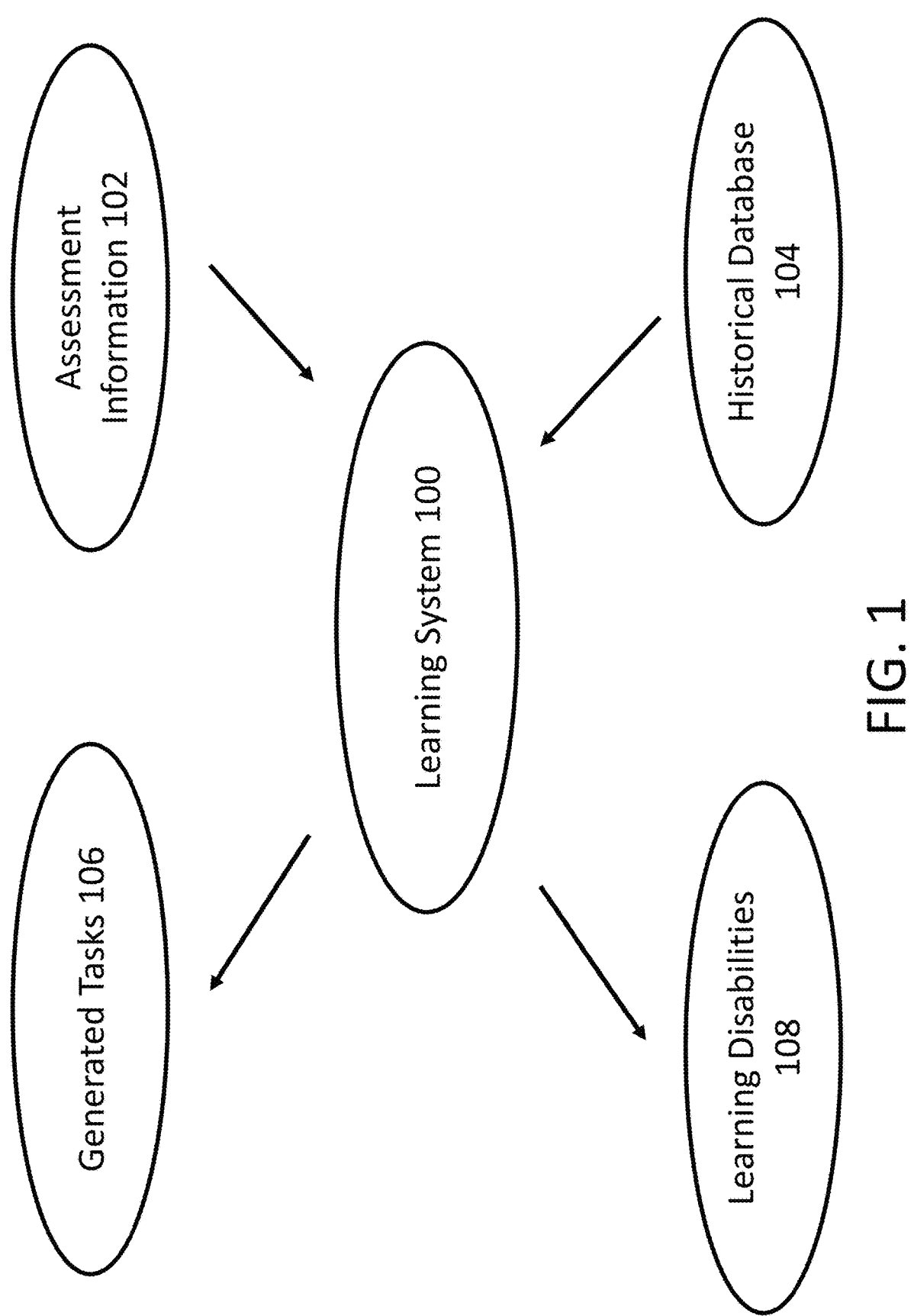
FIG. 1 is a diagram of an example flow diagram.

The following detailed description refers to the accompanying drawings. The same reference numbers in different drawings may identify the same or similar elements.

Systems, devices, and/or methods described herein an electronic communication system that is used as an electronic educational tool (e.g., a learning system) to assist in achieving educational goals of young children. In embodiments, the learning system can recalibrate and individualize the attention to each student. In embodiments, the learning system includes an online screening tool. In embodiments, the screening tool can be used to assess and evaluate a child's language skills which can then be used by a teacher to make informed decisions on the level of each student.

In embodiments, the learning system can predict, based on speed and accuracy of processing and performance, a range of reading difficulties, including reading difficulties that are pedagogical in nature. In embodiments, the learning system can also predict additional reading disorders that include developmental and also dyslexia, dysgraphia and spelling disorders. In embodiments, the learning system uses analytical reports and charts to present student performance data on the reading skills assessments. In embodiments, the learning system enables teachers to benchmark the student's results against previous assessments taken and to also compare them against their peers who are in the same age group or grade level.

Accordingly, the learning system evaluates the level of the student and flag learning gaps. It does that through having the student go through a series assessments comprised of 13 to 16 tasks depending on grade level. In embodiments, the assessment is taken online using a microphone and headphones and allows the student to pause and continue the assessment at each assessment section, thus having the option of conducting the assessment in multiple stages rather in one go. In embodiments, the assessment assesses the student (e.g., the user of the learning system) in by giving the sample tasks and explanations on what is expected from them thus ensuring the clarity of instructions.

In embodiments, once the full assessment is completed, the teacher or administrator receives the assessment report results for the review and analysis. This will enable the teacher to update the kind of learning support as required by being provided with updated tasks via the learning system. Accordingly, this makes education more individualized in a way that every child gets the information they may need be on the required level in comparison to their peers.

In embodiments, the learning system evaluates oral reading skills, phonological awareness, naming speed, verbal sort term memory, orthographic and spelling knowledge, and written and spoken comprehension. In embodiments, the learning system uses artificial intelligence (AI) to evaluate student responses and to provide real-time scores. In embodiments, the learning system includes (a) an online assessment, (b) predesigned tasks, (c) real-time assessment results, (d) comparison to other results, (e) store historical data, and (f) provide a diagnosis of student learning difficulties. By doing so, the learning system can in real-time automatically determine a student's learning abilities by receiving electronic information from multiple users at the same time. Accordingly, the learning system reduces computing resources that would be needed at each location and reduces the needs for independent computing systems as well as reducing computing memory resources.

FIG. 1 is an example flow diagram of system 100. As shown in FIG. 1, learning system 100 can receive electronic information and, based on the electronic information, generate one or more tasks as well as determine parameters relating to learning disabilities. In embodiments, learning system 100 may be one or more computing devices that in real-time assessments, compare assessments to stored historical data, and provide various types of analysis of electronic information. By doing so, learning system 100 reduces computing memory and resources that are used to assist in teaching one or more skills As shown in FIG. 1, assessment information 102 is electronically sent (e.g., via a type of communications network such as the Internet) to learning system 100. In embodiments, assessment information 102 includes electronic information based on assessing one or more individuals. In embodiments, assessment information 102 includes different characteristics of an assessment. These different characteristics includes (a) number of words spoken correctly, (b) the speed at which words are spoken during a period of time, (c) number of words read correctly, (d) the speed at which words are read during a period of time, (e) information how words are used within a sentence, (f) whether words are correctly spelt and the number of words are correctly spelt, (g) whether syllables are spoken correctly, (h) naming numbers correctly, (i) assessment of the person's short term memory, and/or (j) psychological awareness. In embodiments, the collected dataset may be from schools targeting students from grade 1 to 6 with all necessary data, including recordings, speed, and time logs for each student and task. Furthermore, the collected data encompassing a variety of speakers, accents, environments, and speaking styles.

As shown in FIG. 1, learning system 100 also receives electronic information from historical database 104 which includes one or more databases with previous assessment information about other individuals. In embodiments, historical database 104 may include information about what would be considered normal for a person of a particular age. In embodiments, the electronic information obtained from historical database 104 may be based on the historical electronic information from a person who is of similar age to the person for whom the electronic assessment information was conducted for.

Based on the electronic assessment information and the information received from historical database 104, learning system 100 determines generated tasks 106. In embodiments, generated tasks 106 include one or more tasks that are electronically displayed on a computing device and can be used by a person to learn a particular task. In embodiments, generated tasks 106 may be (a) one or more sentences displayed for reading, (b) an electronic display that includes providing missing words within a sentence, and (c) an audible question which requires the person to provide a verbal or written response.

Also, as shown in FIG. 1, learning system 100 also generates learning disabilities 108. In embodiments, learning disabilities 108 are the determination of learning system 100 of various reading difficulties, including reading difficulties that are pedagogical in nature (e.g., related to teaching). In addition, learning system 100 may also determine, based on the historical database 104 and assessment information 102, reading disorders that are developmental, dyslexia, dysgraphia and spelling disorders.

In embodiments, the determination of a learning disability is based on the tasks structured to check for particular multi-factors. In embodiments, the described tasks can be taken in any order and are independent from another task. While the described tasks are independent of each other, the tasks analysis is inter-related since factors can be tested in different tasks. In embodiments, FIG. 48 describes example tracked factors analyzed from student responses for each task. For example, as shown in FIG. 48, when analyzing a response to an orthographic decision, the learning system analyzes the factors of phonology, orthographic, and speed. For example, a student may answer the Arabic letter سـ correctly in task 1 however miss the same Arabic character ـسـ when it is in the middle of the word.

Figure 2A:
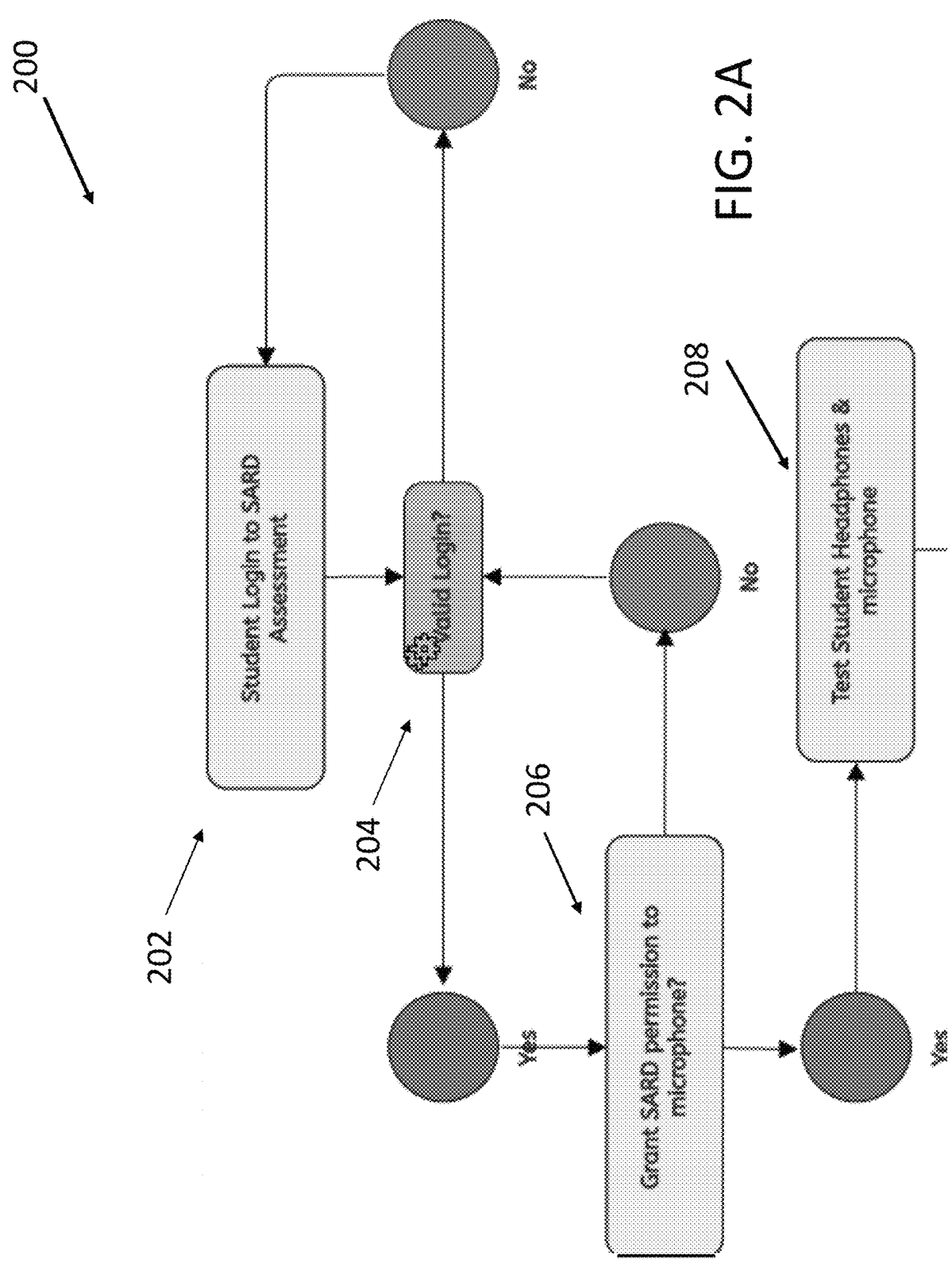
FIGS. 2A and 2B are diagrams of example flowcharts.
Figure 2B:
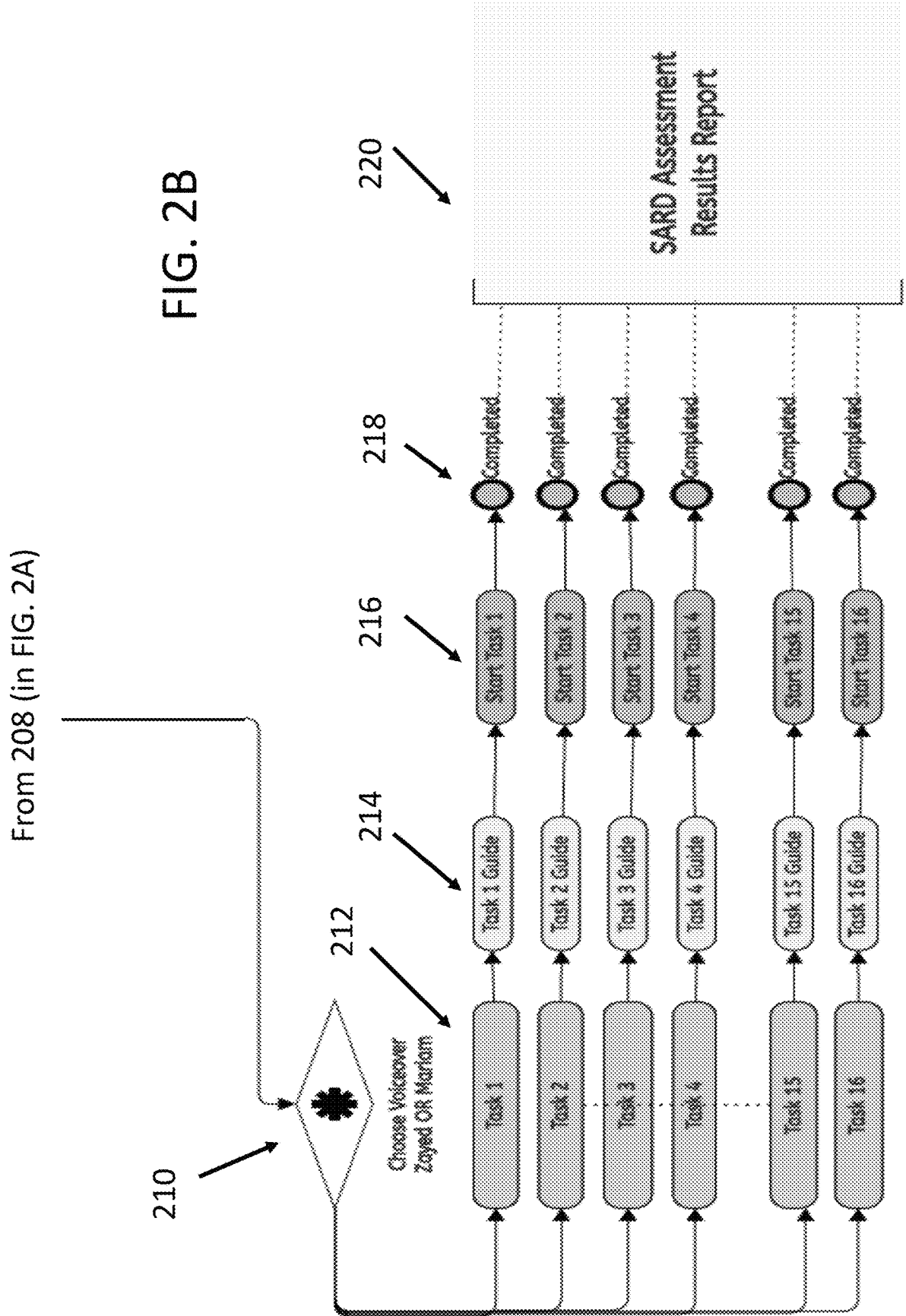

FIG. 2 describes example flowchart 200. In embodiments, flowchart 200 may be conducted by learning system 100. As shown in FIG. 2, at step 202, a user (e.g., a student or someone assisting the student) logs into an electronic application that has a graphical user interface that sends and receives electronic information to/from learning system 100. If the login is not valid (step 204—NO), the electronic application again requests the correct login credentials. If the login is valid (step 204—YES), then, at step 206, the electronic application requests permission to use a microphone of the computing device on which the electronic application is being used on. If permission is not provided by the user (step 206—NO), then electronic application returns to the login area with no additional communication or may provide a message that the user cannot continue with the electronic application.

If permission is provided by the user (step 206—YES), then, at step 208, the electronic application tests the computer device's microphone and the headphone being used by the user. In embodiments, the test determines that the user's spoken words are being correctly recorded by the electronic application based on the electronic information being provided in a verbal format and heard by the user via the headphone.

At step 210, the electronic application provides a choice to the user on which electronic voice the electronic application will use to communicate with the user during the testing process. In embodiments, the user can choose between a male sounding voice or a female sounding voice.

At step 212, the electronic application provides a task. As shown in FIG. 2, there are multiple tasks up to task 15; however, in other instances, there may be greater or fewer than 15 tasks and 15 tasks is provided as an example. In embodiments, the task (e.g., task 1) is presented to the user. At step 214, a task guide (e.g., task 1 guide) is provided to the user. In embodiments, the task guide may be electronic verbal communications to the user by the electronic application. Alternatively, the task guide may be written words displayed by the electronic application.

Once the user has understood the task guide (e.g., by clicking on an icon generated by the electronic application), at step 216, the task is started. As described in FIG. 1, the task may be a reading task in which the electronic application displays one or more sentences for the user to read into the microphone which is then picked up by the electronic application. Alternatively, the task may be a spelling task in which the electronic application electronically generates an audible word and the user is requested to use the keyboard to sell out the spoken word. Alternatively, the task may be entering words missing in a displayed sentence generated by the electronic application.

At step 218, the task is completed by the user. In embodiments, the task may be completed within a particular amount of time. In embodiments, the particular amount of time may be used by the learning system (e.g., learning system 100) to determine if the user has any learning disabilities. At step 220, the electronic information about the completed task is sent to the learning system. In embodiments, the learning system analyzes the completed task and analyzes the results for any issues with the completed task. For example, the learning system may determine whether mistakes were made during the task, such as spelling mistakes or mistakes relating to the pronunciation of a word. In embodiments, the learning system may determine if the task was completed within a particular amount of time. In embodiments, based on the analysis of the completed task, the learning system generates an electronic report that is displayable via the electronic application (or may be sent to another computing device in a document file that can be downloaded on the other computer or a click on a hyperlink).

In embodiments, the electronic report may describe one or more issues relating to the completed task. For example, the electronic report may include information about learning disabilities relating to the user based on how the completed task was completed. The electronic report may also include information about different tasks that are to be completed by the user. For example, the user may be provided with one or more different tasks.

Figure 3A:
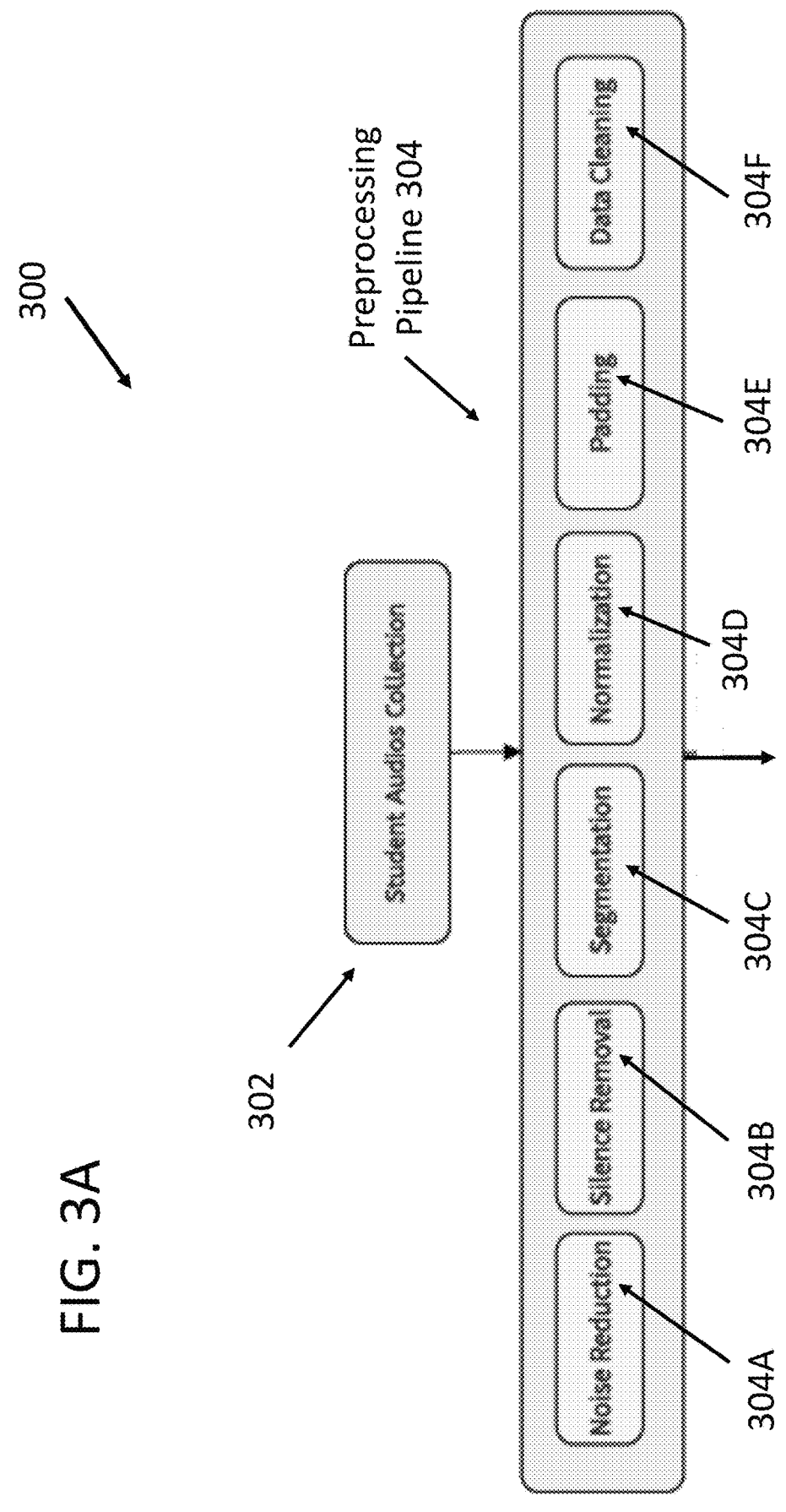
FIGS. 3A and 3B are diagrams of example flowcharts.
Figure 3B:
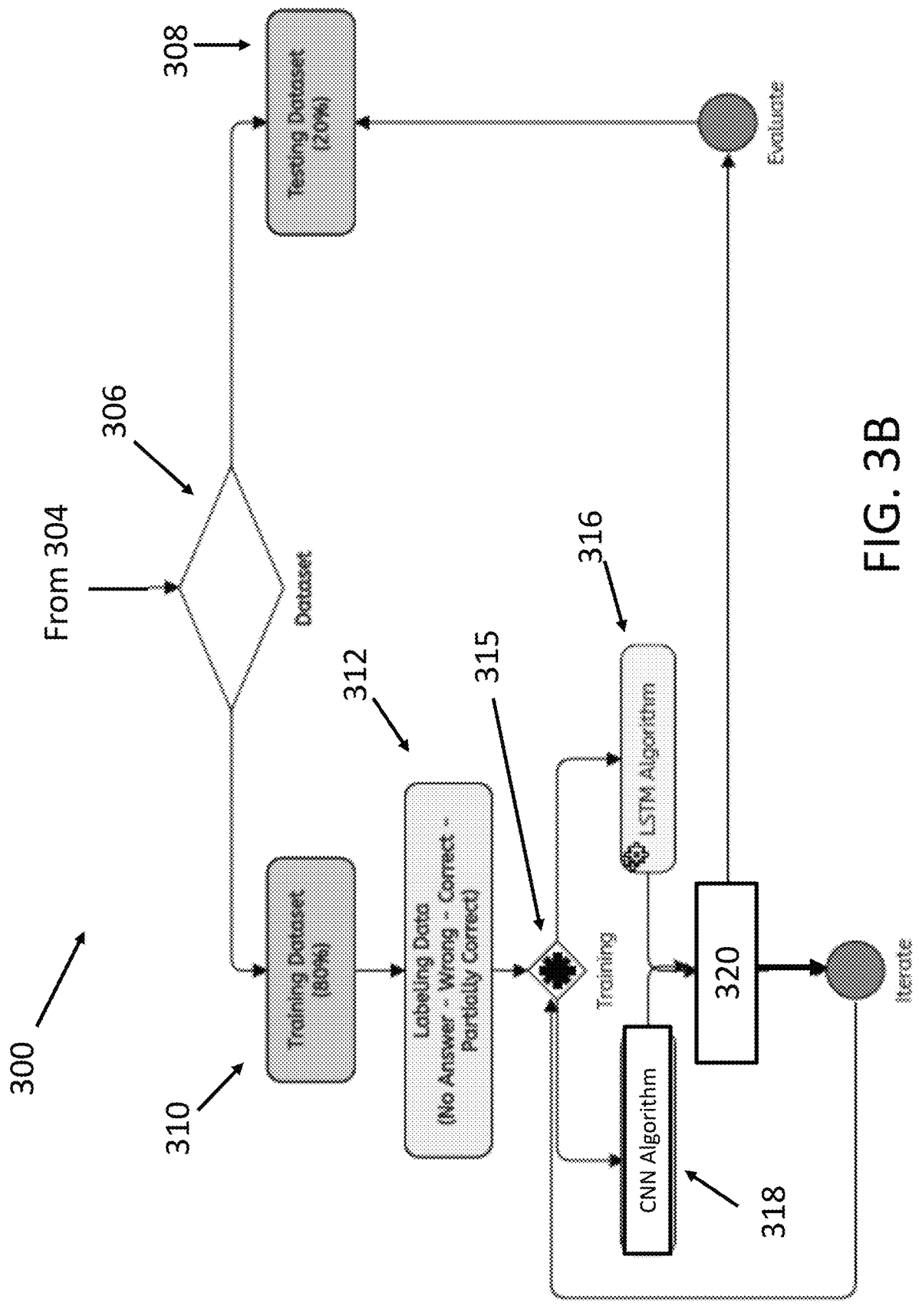

FIGS. 3A and 3B describe flowchart 300. In embodiments, flowchart 300 describes the process of how a learning system analyzes completed tasks (such as discussed for FIGS. 1, 2A, and 2B) and determines solutions to assist a user's learning behavior.

As shown in FIG. 3A, at step 302, audio collection of one or more users is received by the learning system (e.g., learning system 100). In embodiments, the audio is generated by the one or more users when they perform one or more tasks, such as reading numbers and/or words. In embodiments, once the learning system has received the electronic audio information, at step 304, the learning system performs preprocessing (i.e., the preprocessing pipeline) onto the electronic audio information.

As shown in FIG. 3A, preprocessing includes noise reduction 304A, silence removal 304B, segmentation 304C, normalization 304D, padding 304E, and data cleaning 304F. In embodiments, noise reduction 304A reduces noises that occur when a student is providing an answer via the microphone. In embodiments, at the beginning of the assessment, a sample audio spectrogram is collected from the student to test the microphone and headphones. In embodiments, the spectrogram feature of these recordings is used to compare it with later recorded audios to reduce noise. This may also occur when students take their assessment during school breaks or the teacher did not maintain the required space between students.

In embodiments, silence removal 304B may be used during a text reading text. In embodiments, user recorded responses (when converted to sound waves) may include sound wave slots in a time T with a null frequency. In embodiments, these sound wave slots in a time T with a null frequency represents silence and has no effect on classifying a speech. In embodiments, to exclude such unneeded data (i.e., the wound wave slots with a null frequency) from being inputted to the training model, these particular types of wave slots with no recorded frequency are removed. By removing the wave slots, this reduces the model training processing time and generalizing on model output. In embodiments, segmentation 304C, tasks with pre-defined timespans are segmented into smaller audio clips based on the set timespan seconds. This is because, each timespan should contain a phrase that answers the question. Accordingly, an input for training the model is based on equal length input because the task question will be displayed for specific amount of time (e.g., in seconds) and then a new question appears until the end of task. Thus, the student response is recorded automatically without any intervention from the student. For example, having 20 questions with timespan of 2.5 seconds per question results in 50 seconds total response time. Then, the wave is segmented to 2.5 seconds equal splits where each split is processed as an input to the model. This can also be seen when the timespan for some tasks is extended after we noticed that majority recorded responses resulting as wrong answer after segmentation was applied. Because, the resulted splits showed an in-complete sound wave. For example, originally the question shows the word بيت for two seconds, however the recorded response wave has active frequency last over 2.5 seconds. Thus doing the segmentation at 2 seconds will cut the student response and resulting in wrong answer classification. In embodiments, normalization 304D, the volume is normalized across all recordings to ensure consistent volume levels. In embodiments, padding 304E. In embodiments, silence padding 304E is added at the start and end after segmentation to prevent clipping any data. Moreover, tasks with a non-pre-defined timespan, the task response will be recorded until the user of the learning system submits the response. Thus, each of the user's responses are of varied length, and this is different from pre-defined timespan tasks. In order to maintain equal wave inputs to our model, zero padding is added to the wave but with no effect on the classification. Accordingly, this will maintain equal number of inputs with all responses In embodiments, data cleaning 304F, all audios labeled as "No Answer" are excluded from the dataset.

FIG. 3B provides further description of flowchart 300. Once the preprocessing of the electronic audio information is conducted, at step 306, the learning system determines a dataset. As shown in FIG. 3B, that a training dataset and a testing dataset are generated. As shown in FIG. 3, the training dataset is determined to be 80% of the data while the testing dataset is determined to be 20%. In other examples, the percentages of the training and testing datasets may be different (e.g., 70% of training dataset and 30% of testing dataset).

At step 312, electronic information in the training dataset is labeled. In embodiments, the label can be "no answer," "wrong," "partially correct," and "correct." Once each electronic information in the training dataset is labeled, the learning system conducts training. In embodiments, the learning system includes an LSTM algorithm which is run at step 316 and a CNN algorithm which is run at step 318. At step 316, the learning system applies a Long Short-Term Memory Networks (LSTM) algorithm is applied to "Reading Text" task to maintain the dependencies between words as a sentence and overcome the correction done by students for some words. At step 318, the learning system takes as input all the sampled student recorded answers in order to be classified into most likely letters and thus converted to text to be compared with the question text and result in one of the following categories: Correct, Partially Correct, or Wrong.

At step 320, the learning system validates the combination of the outputs of steps 316 and 318. At step 320, the learning system validates Word Error Rate (WER) and Character Error Rate (CER) which are metrics used in evaluating speech recognition models. The optimal word and character error rate is zero which implies no errors. Thus, the learnings system uses these training models target to minimize the word and character error rates. In embodiments, these models evaluations resulted in 0.28943 as WER (~28%) and 0.19861 as CER (~19%). Once the learning system validates WER and CER, the output is used to evaluate the testing dataset (at step 308) as well as being used for additional training at step 315. Accordingly, the learning system is able to use the evaluation of the training dataset with the testing dataset to evaluate how well the user performed a particular task. Accordingly, the benchmarks are the results of analyzing all the students' scores and not for training the screening models. The training of the screening models is based on the collection of students' responses. In case the model training leads to better error rates and the generalization on that leads to similar results. In embodiments, the benchmarks can be updated in real-time based on receiving additional responses.

Figure 4:
FIGS. 4-25 are diagrams of example graphs.
Figure 5:
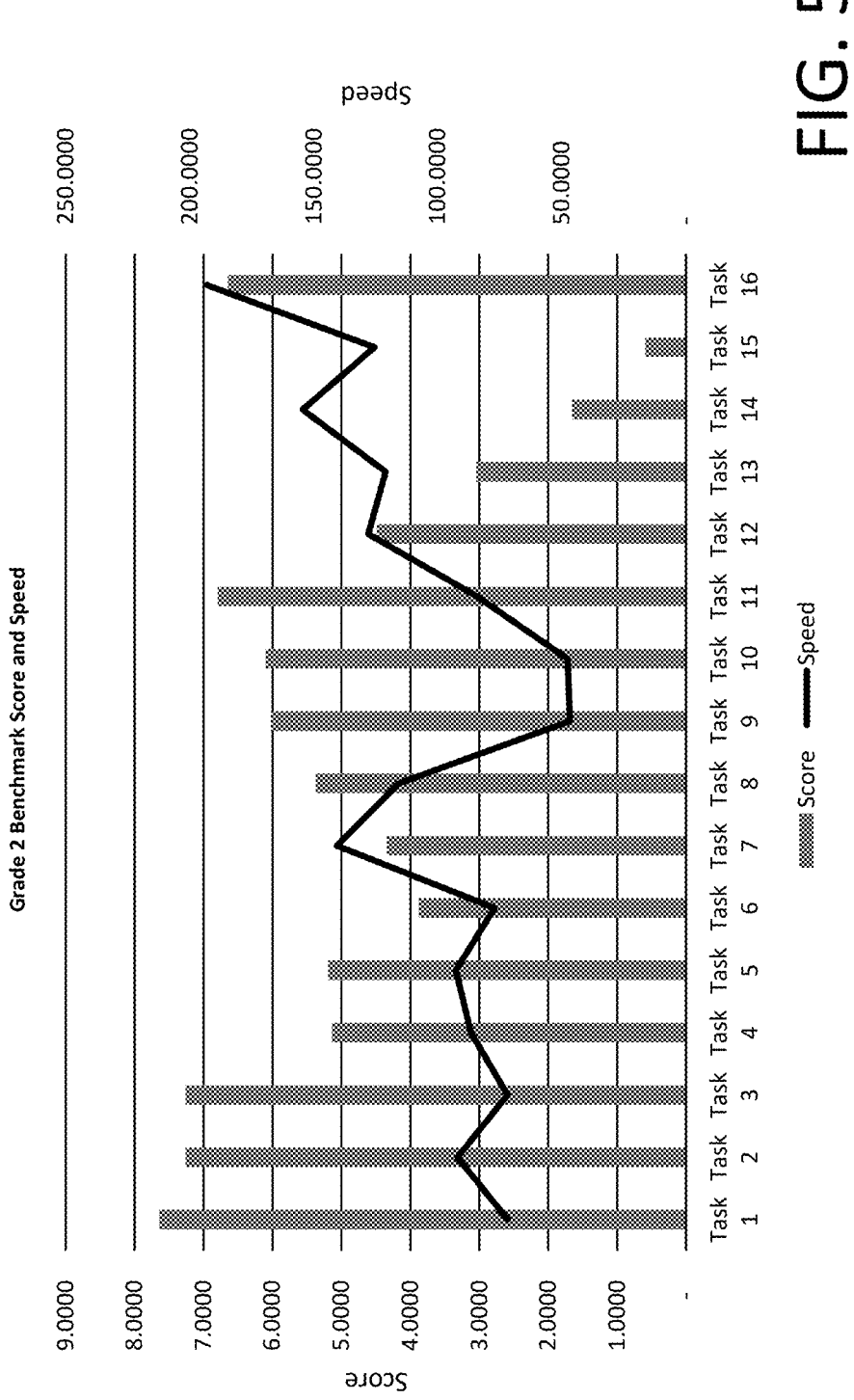
Figure 6:
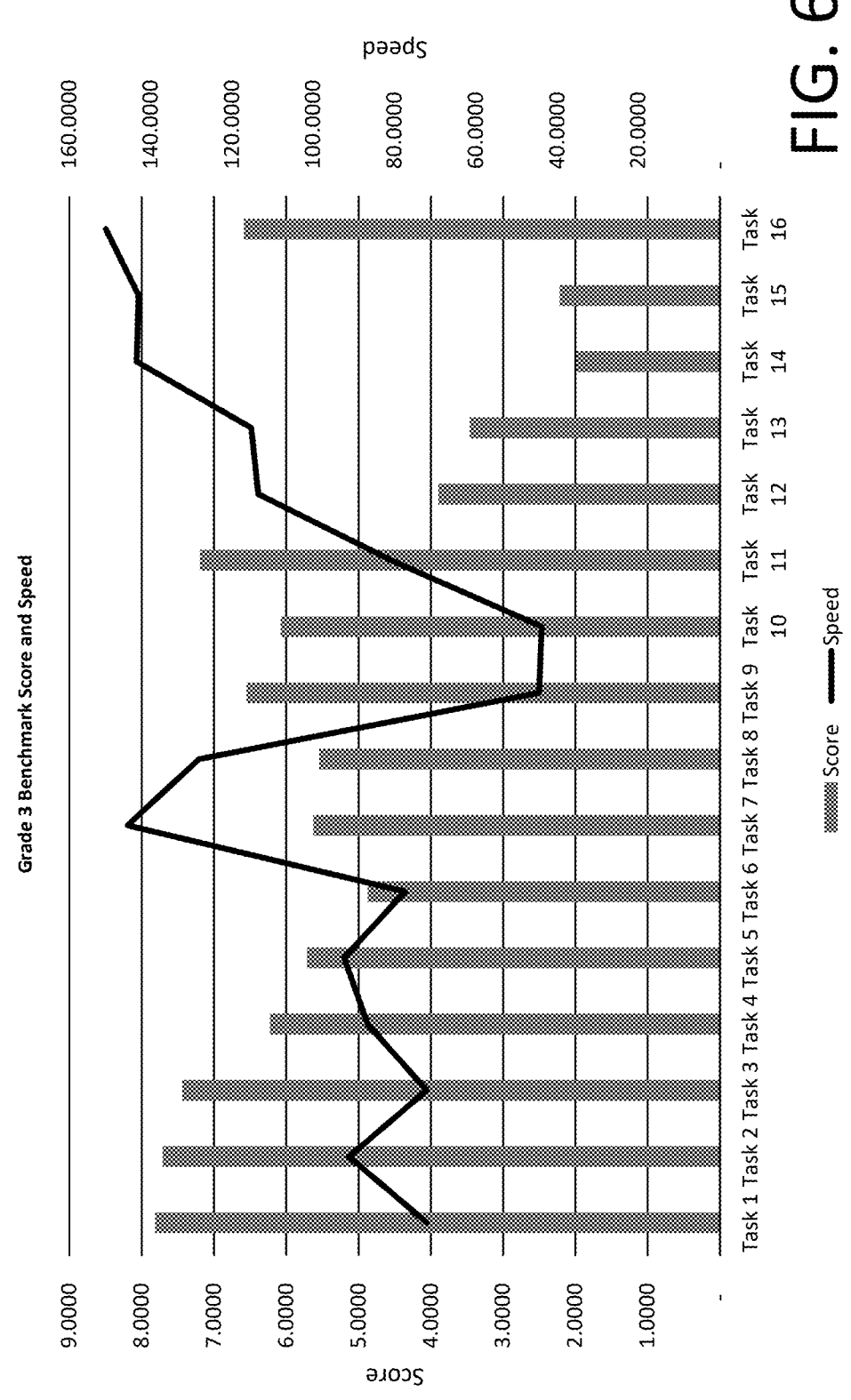
Figure 7:
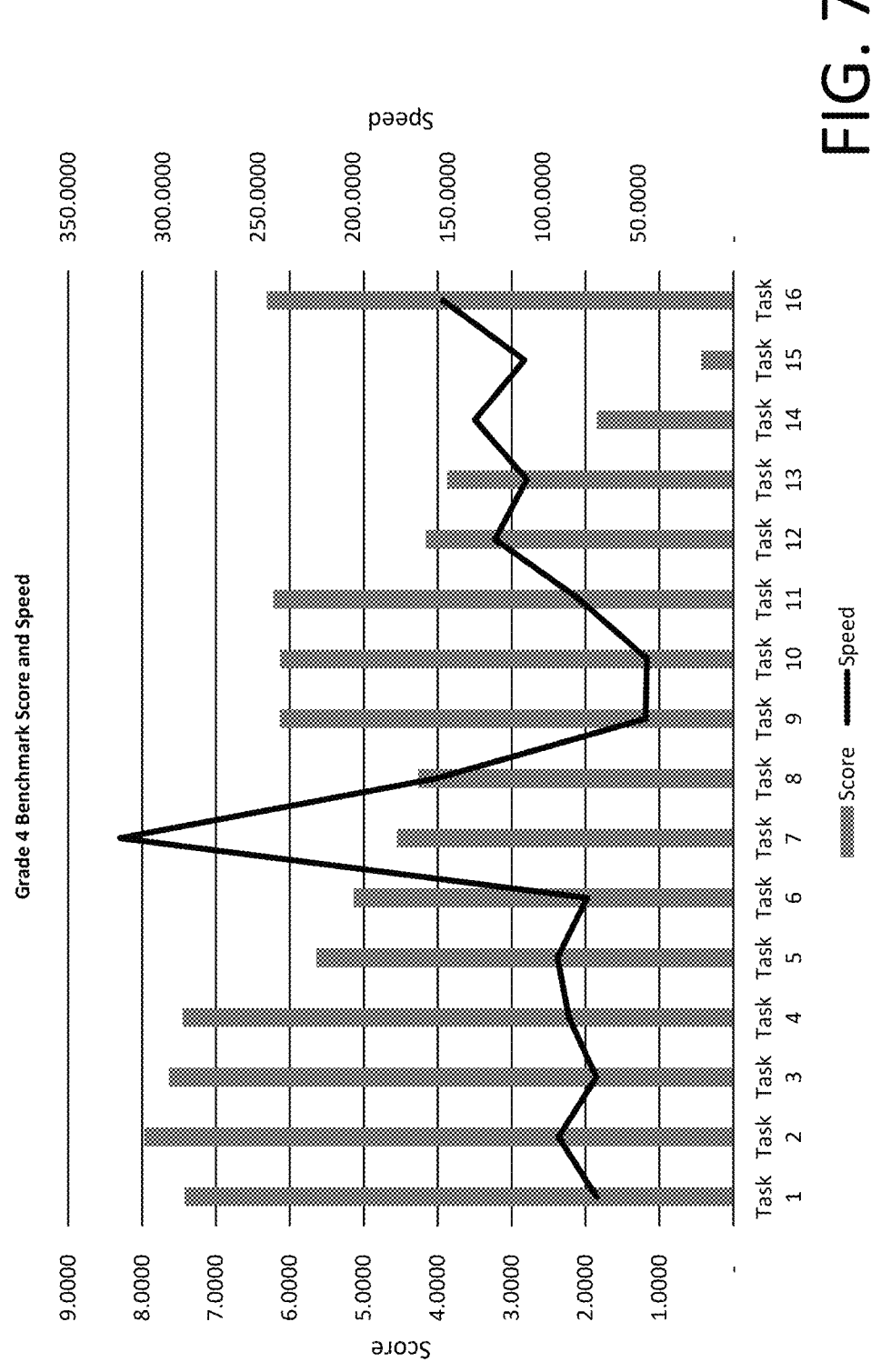
Figure 8:
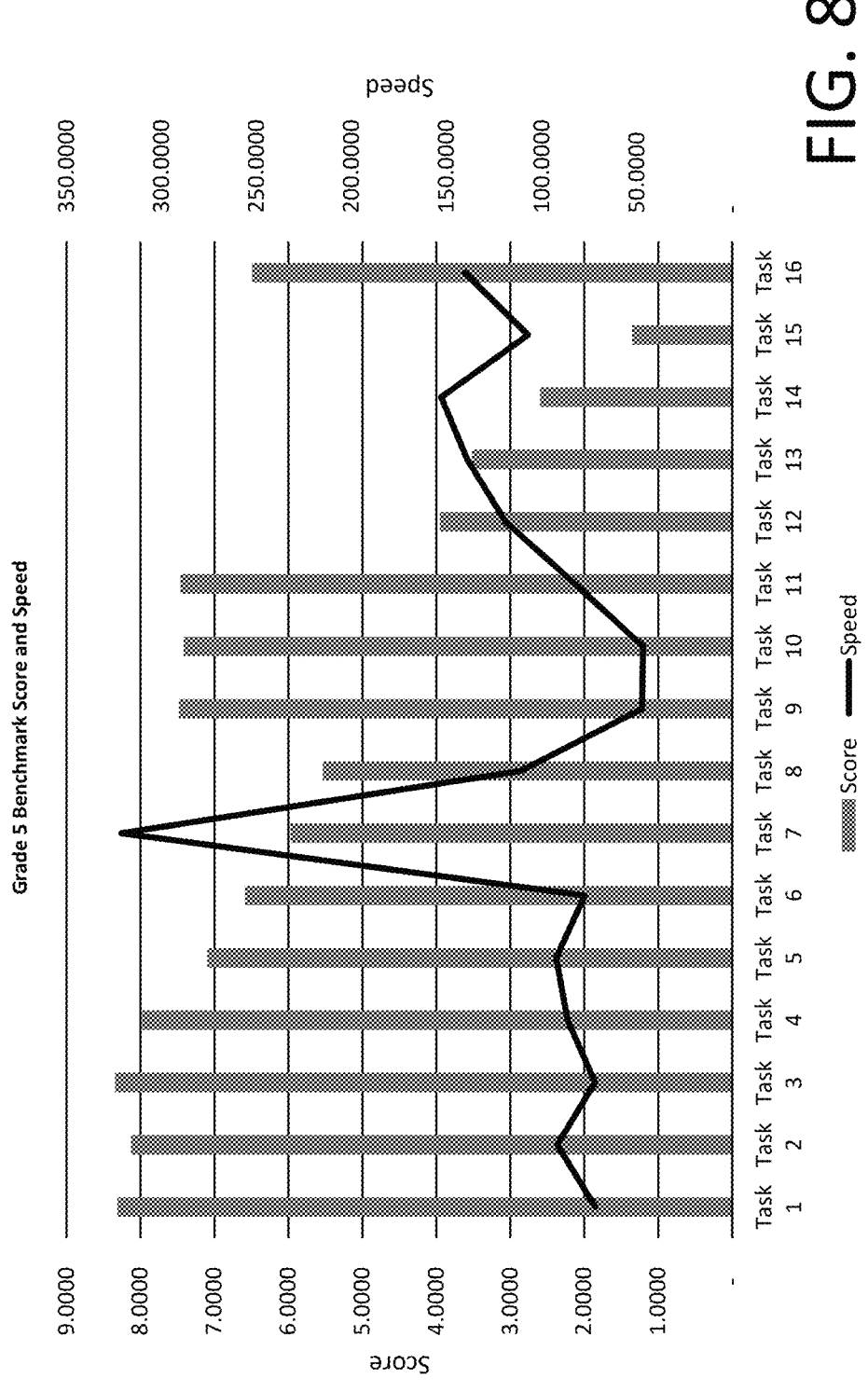
Figure 9:
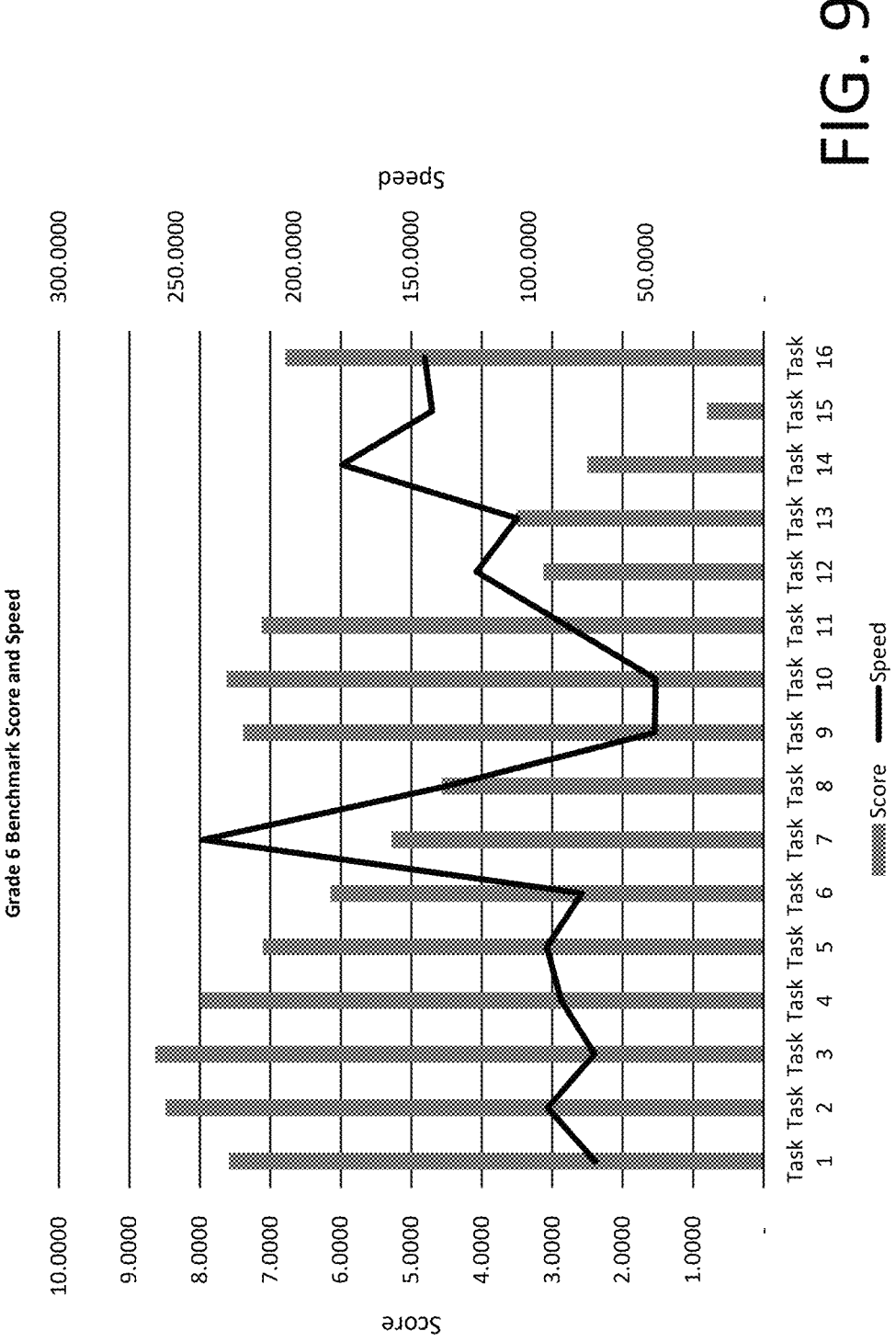
Figure 10:
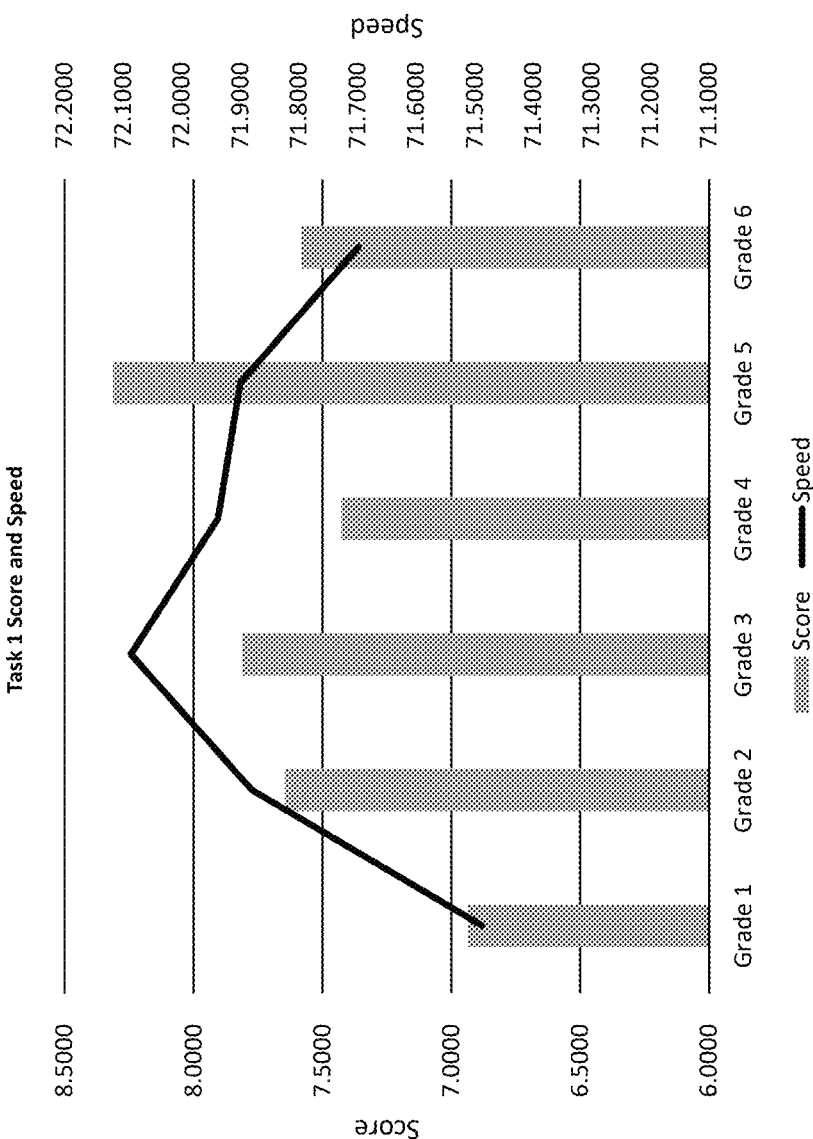
Figure 11:
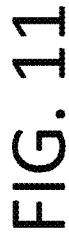

FIGS. 4 to 9 are example graphs that show benchmarking evaluation for particular tasks at a particular grade level. In embodiments, each graph shows a score for a particular task. For example, in FIG. 4, for task 4, a score of 8.0000 is given and for task 5, a score of just above 3.0000 is given. Thus, each figure is shown tasks for a particular grade level (e.g., FIG. 4 is for grade 1 while FIG. 8 is for grade 5.

In addition, each graphs shows a speed assigned to each task. For example, in FIG. 4, for task 4, a speed of just less than 100.00. Accordingly, each task has a benchmark score that is used to determine if the user has performed at a particular level which is considered acceptable. Furthermore, each task has a benchmark speed that is also used to determine that the user has performed the task within a particular amount of time.

For example, a six-year-old child may be given a reading test. In this non-limiting example, the child reads two sentences. The spoken words of the child are converted to electronic form via a microphone and sent to the learning system. In addition, the speed at which the child read the two sentences is also sent to the learning system. The speed may be determined by the electronic application based on when the child starting and then ended speaking. In this non-limiting example, the benchmark score for this task is 5.000 and the speed assigned to this task is 120.00. The child scored 5.500 and the speed was 130.00. Accordingly, while the child scored above the benchmark score, the child was slower in completing the task than the benchmark speed for that task.

In another example, a eight-year-old may be given a spelling test. In this non-limiting example, the child is verbally given three words (e.g., by the electronic application via a speaker) and asked to spell the three words. In this non-limiting example, the benchmark score for this task is 6.100 and the benchmark speed is 110.00. The child scored 6.000 and the speed was 120.00. While the speed is higher than the benchmark speed, the score is less than the benchmark. In instances where either the speed or the score is within a particular threshold of the benchmark speed and/or the score, the learning system may determine that the user has met the benchmark requirements. For example, if the user's speed or the user's score is within 5% of the benchmark speed or the benchmark score, the learning system may determine that the user has met the benchmark requirements.

Figure 12:
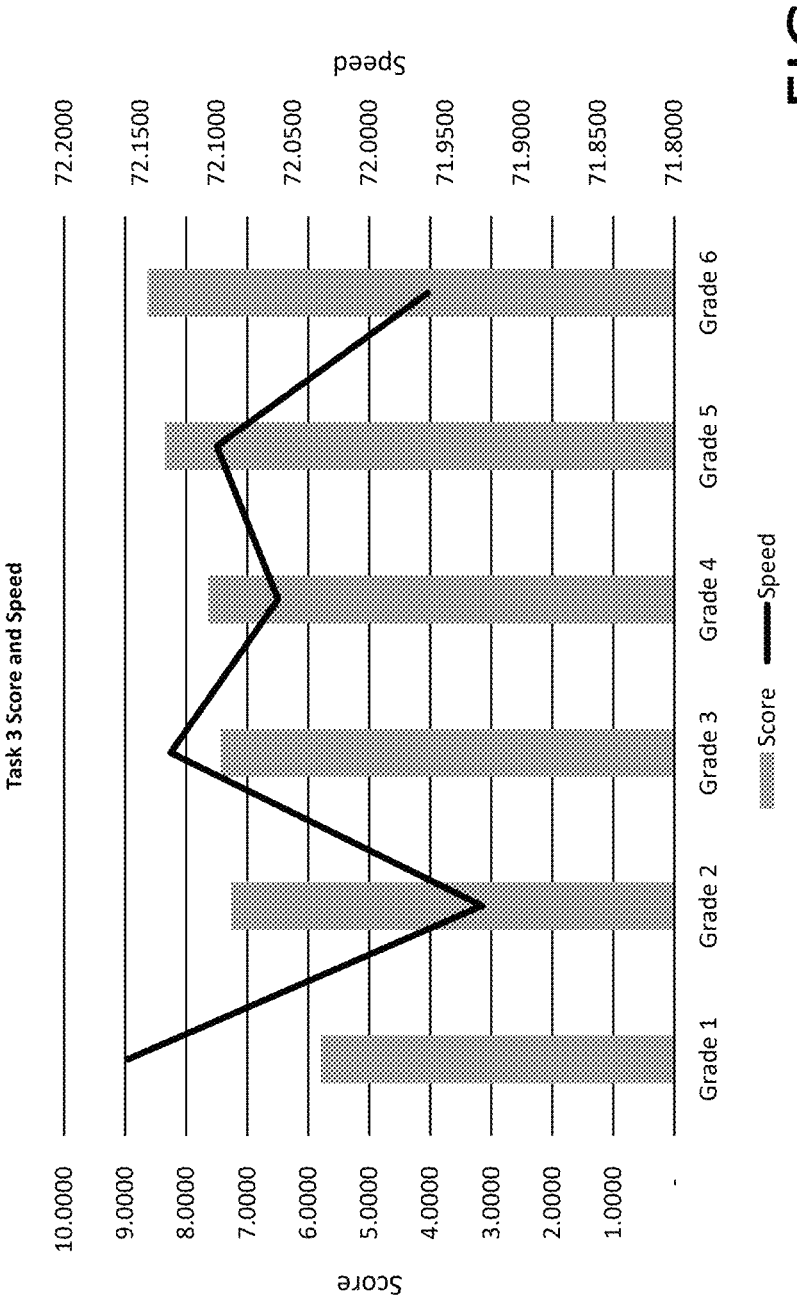
Figure 13:
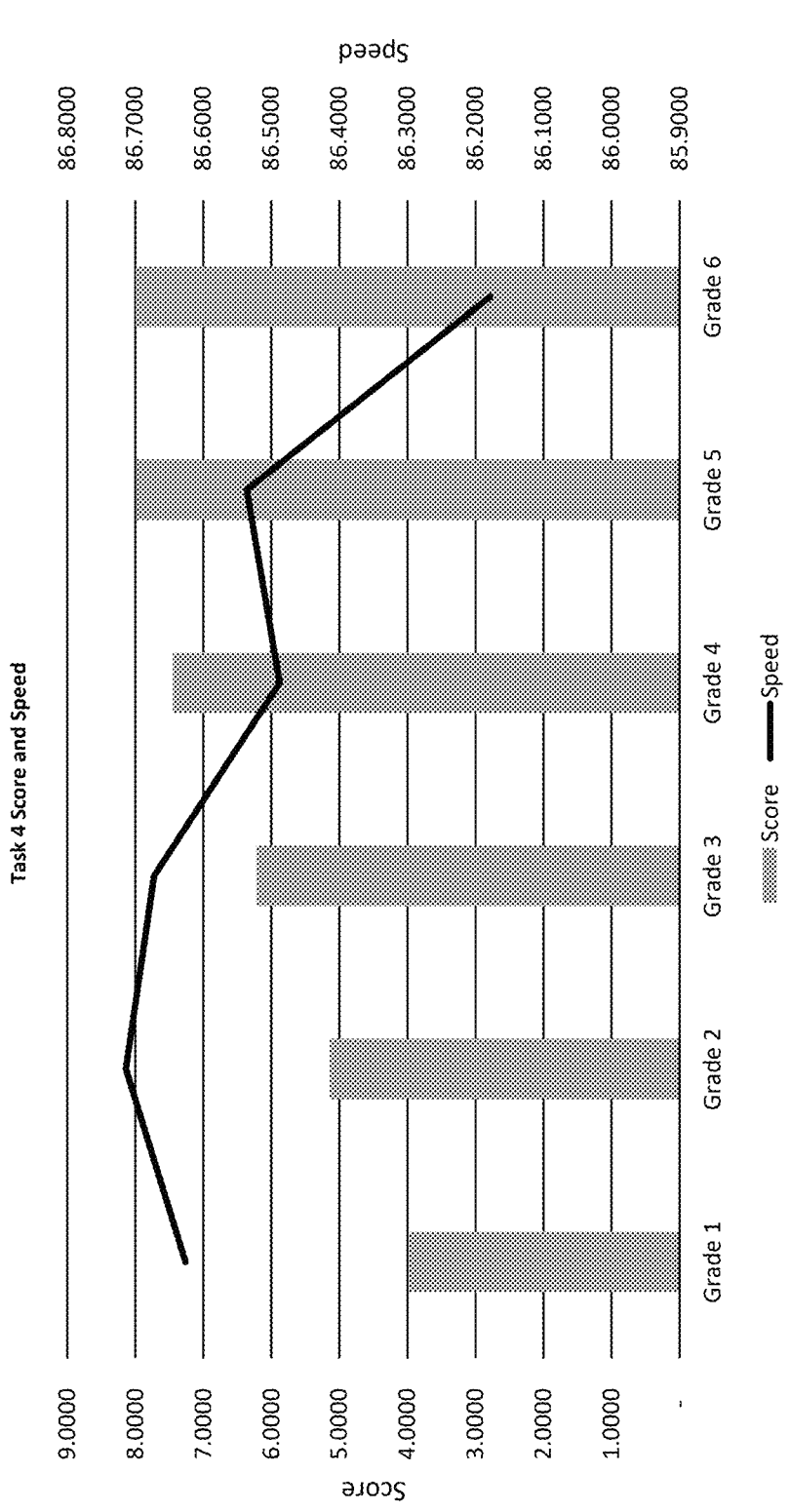
Figure 14:
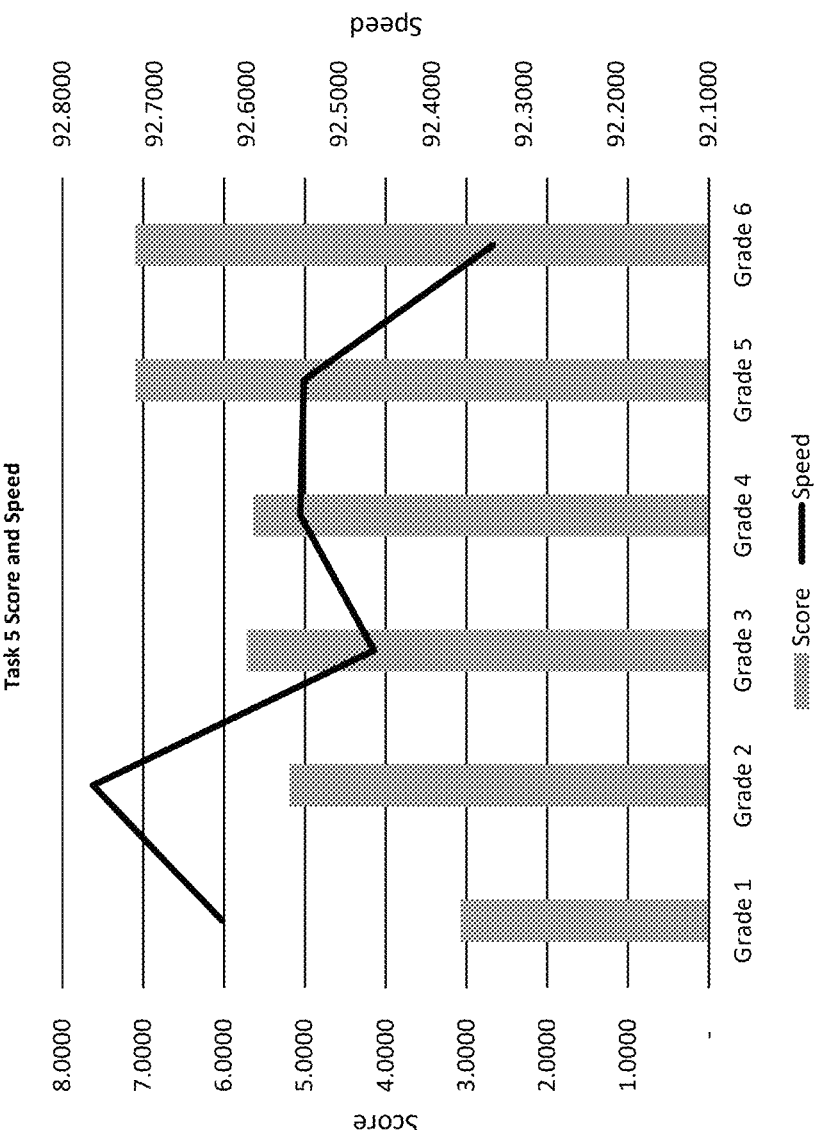
Figure 15:
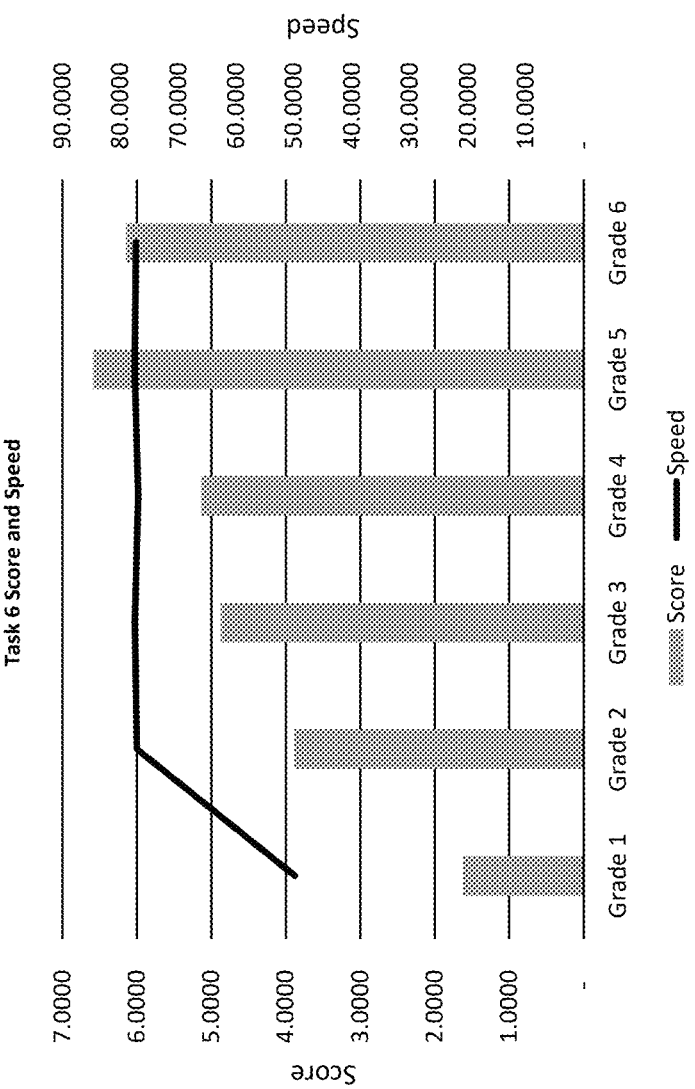
Figure 16:
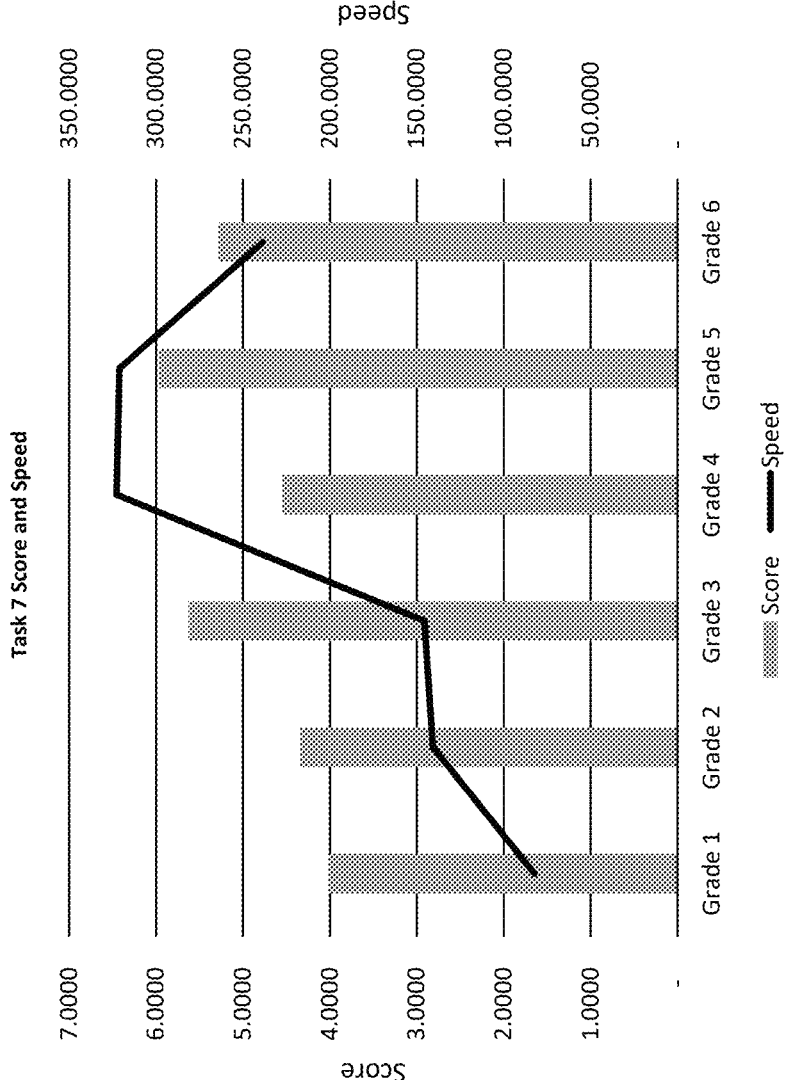
Figure 17:
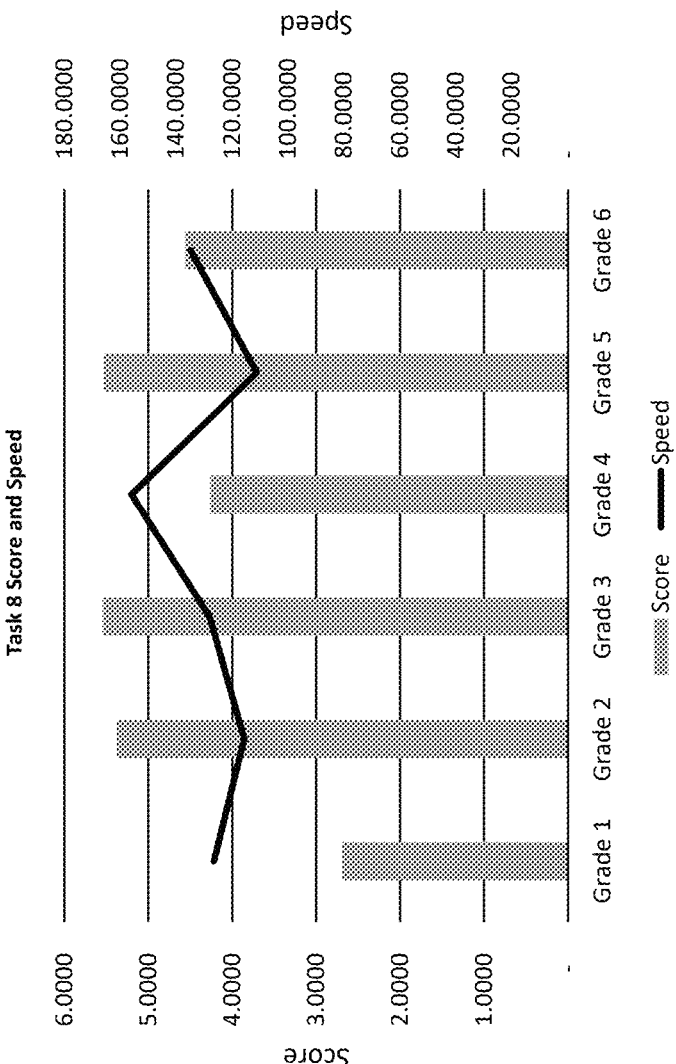
Figure 18:
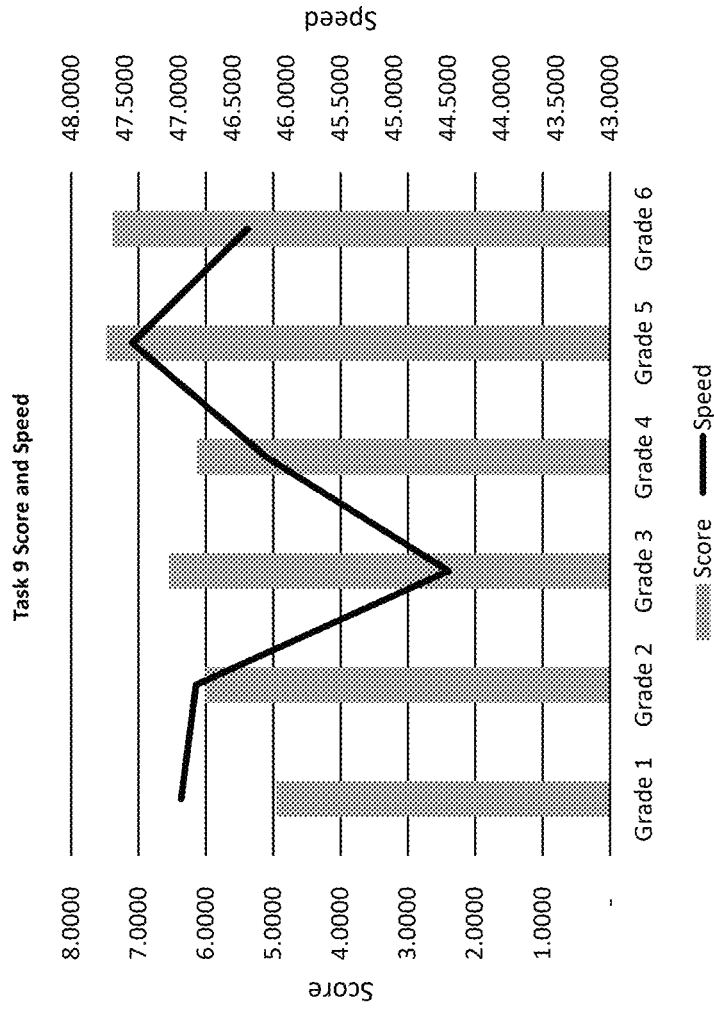
Figure 19:
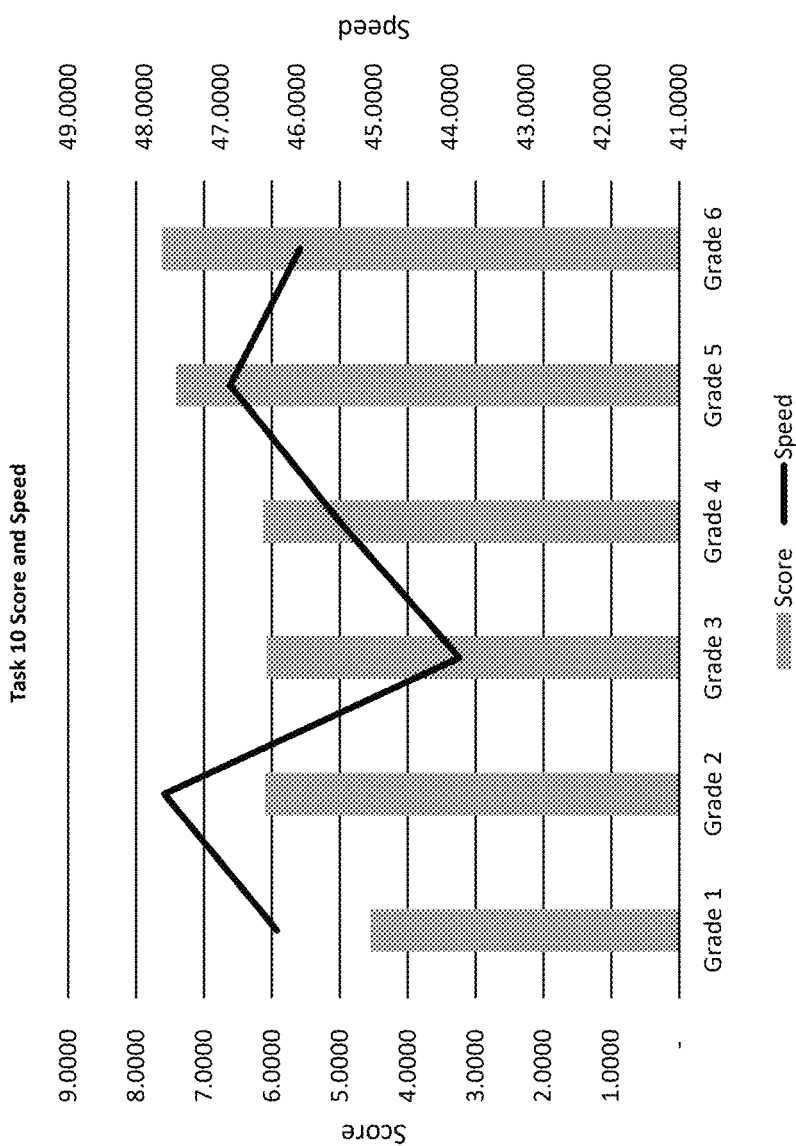
Figure 20:
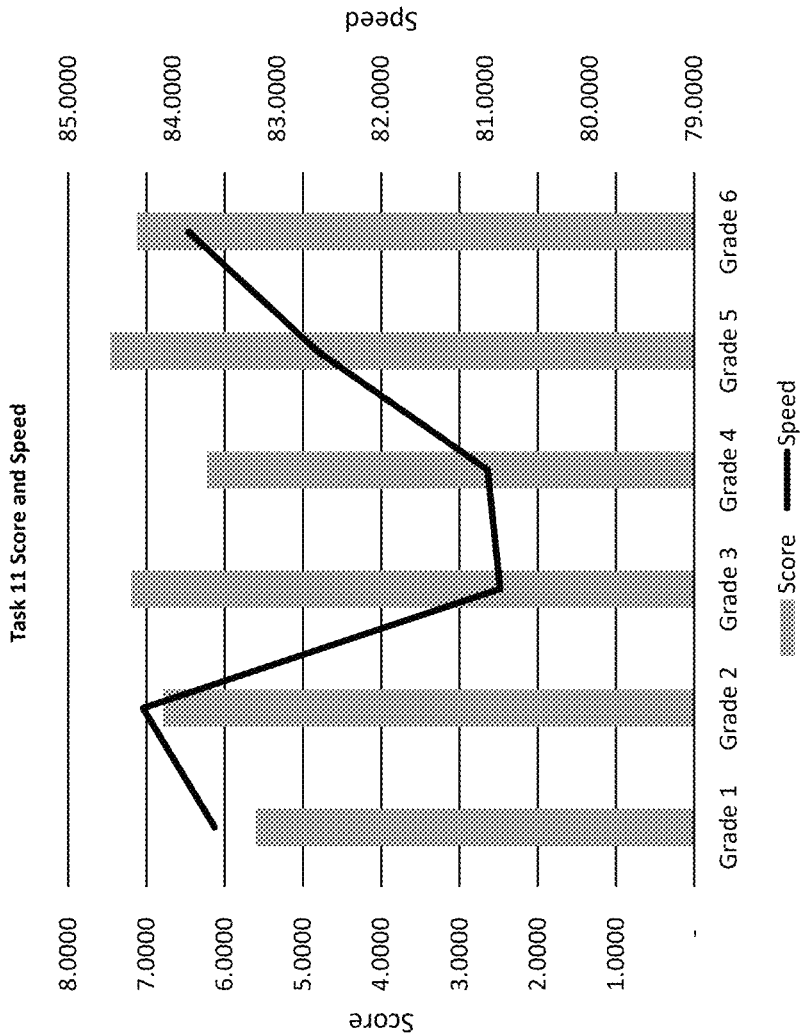
Figure 21:
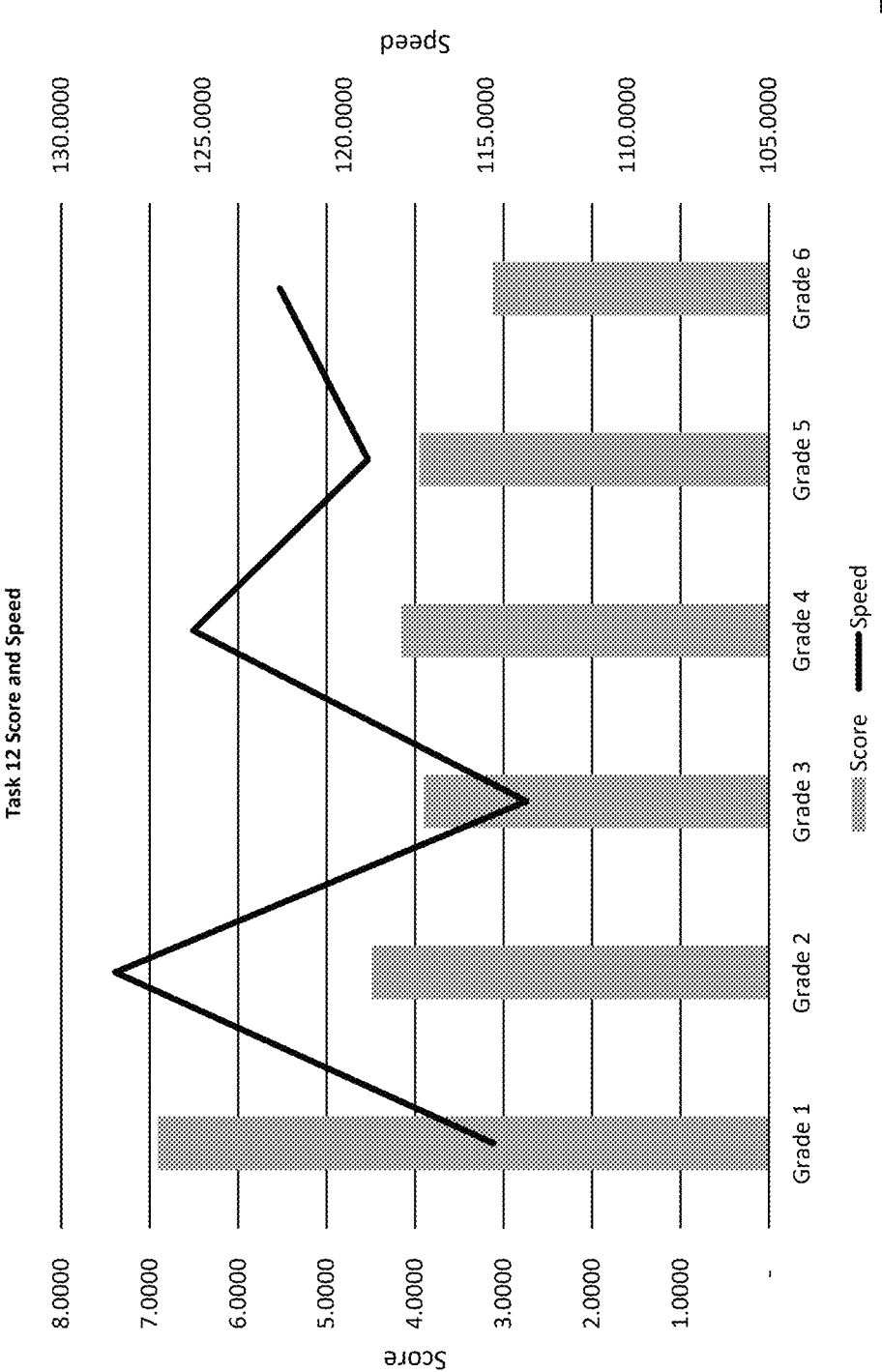
Figure 22:
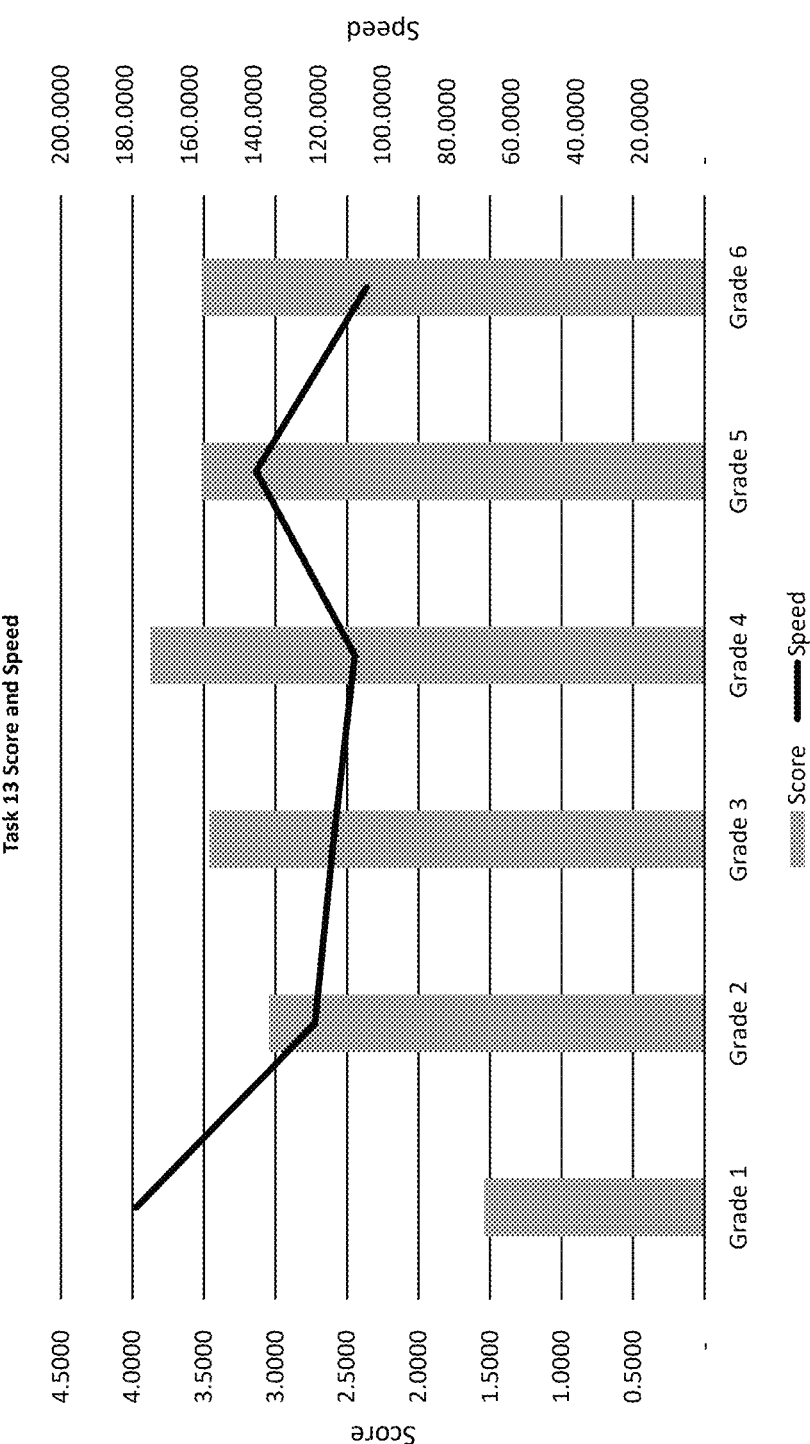
Figure 23:
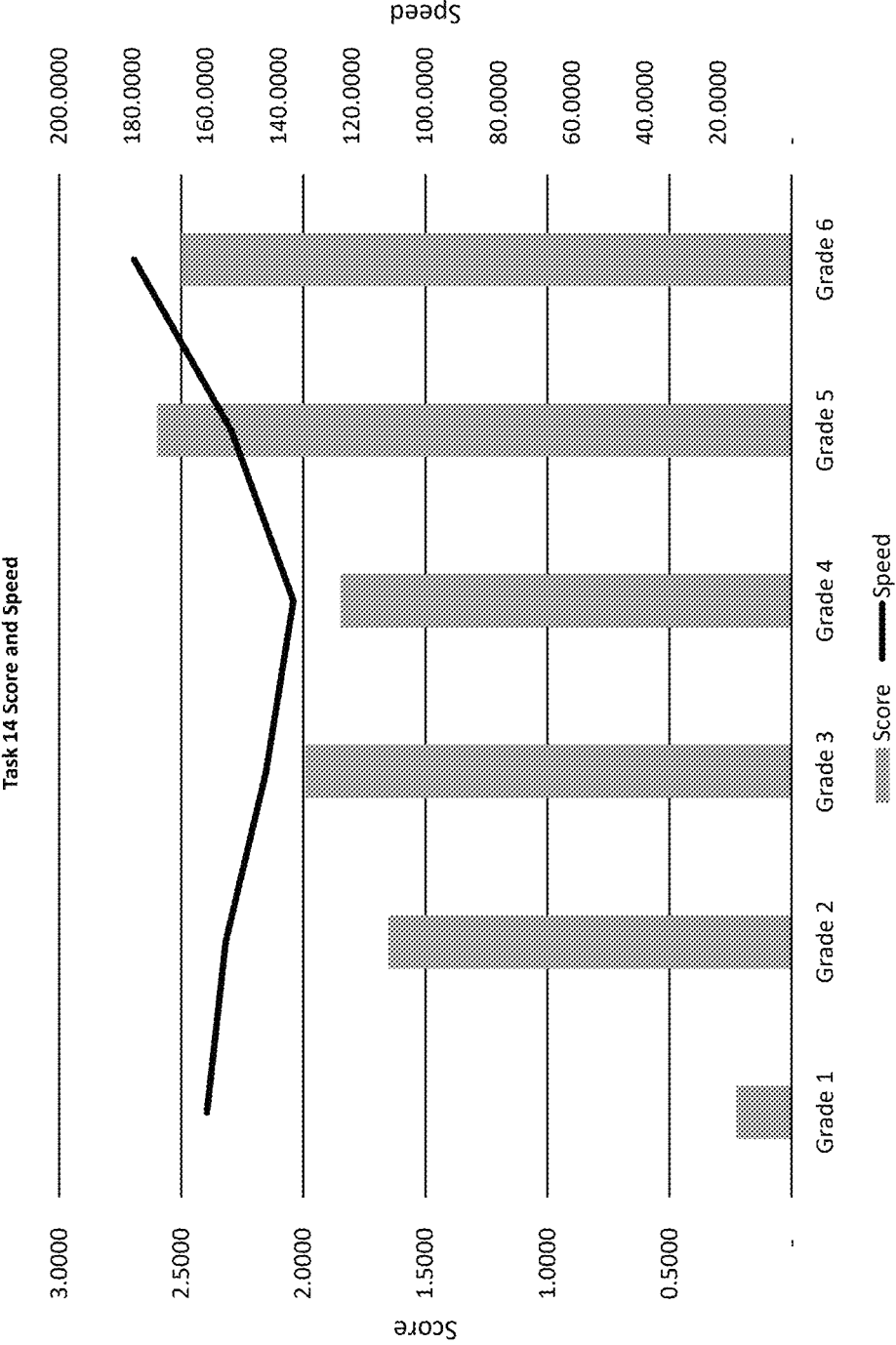
Figure 24:
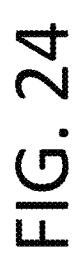
Figure 25:
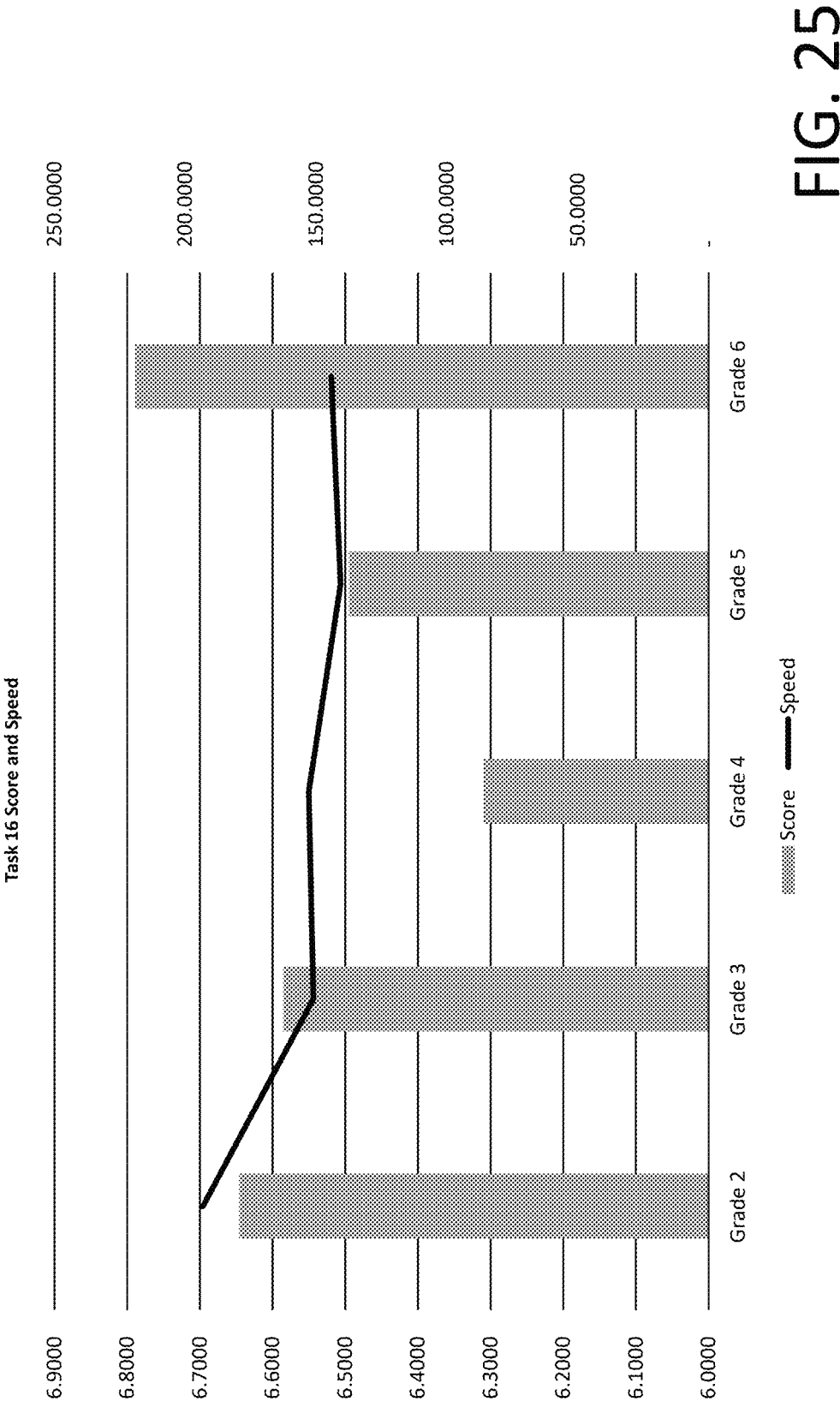

FIGS. 10 to 25 are example graphs that describe scores and speeds for a particular task across different grades. For example, in FIG. 12, for task 3, and for grade 1, the benchmark speed is 72.15 and the benchmark score is between 5.0000 and 6.0000. Accordingly, each task has a benchmark score that is used to determine if the user has performed at a particular level which is considered acceptable. Furthermore, each task has a benchmark speed that is also used to determine that the user has performed the task within a particular amount of time.

FIG. 26 is an example table that describes different tasks and the number of items associated for task. As shown in FIG. 26, the number of items under Items 1 and a different number of items under Items 2. For example, for the task "Reading Real Words," Items 1 is shown as 28 while the Items 2 is shown as 20. In embodiments, each item is for a particular task. For example, for "Number Naming," each item is a number that is to be read by the user of the learning system (e.g., learning system 100). As shown in FIG. 26, the number of items under Items 2 has fewer number of items than the number of items shown under Items 1.

Figure 28:
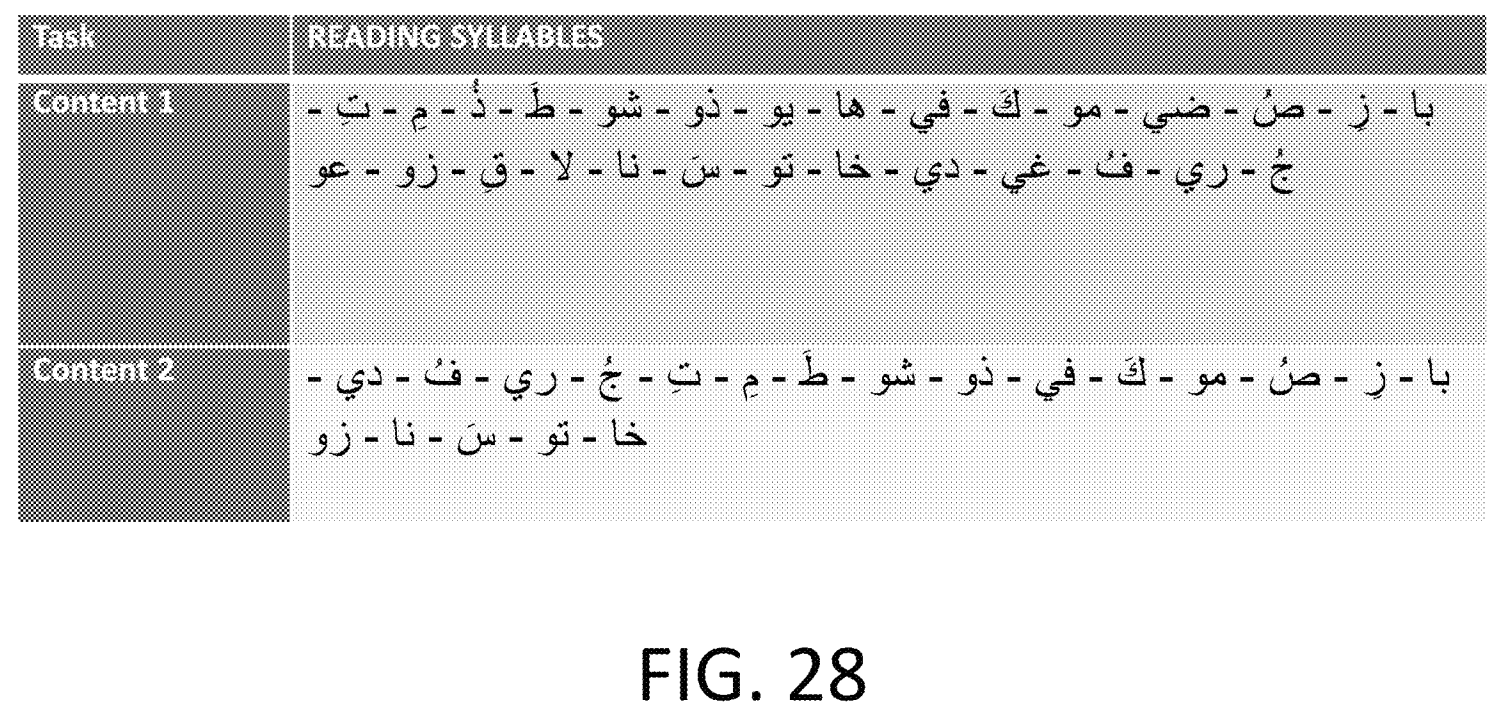
Figure 29:
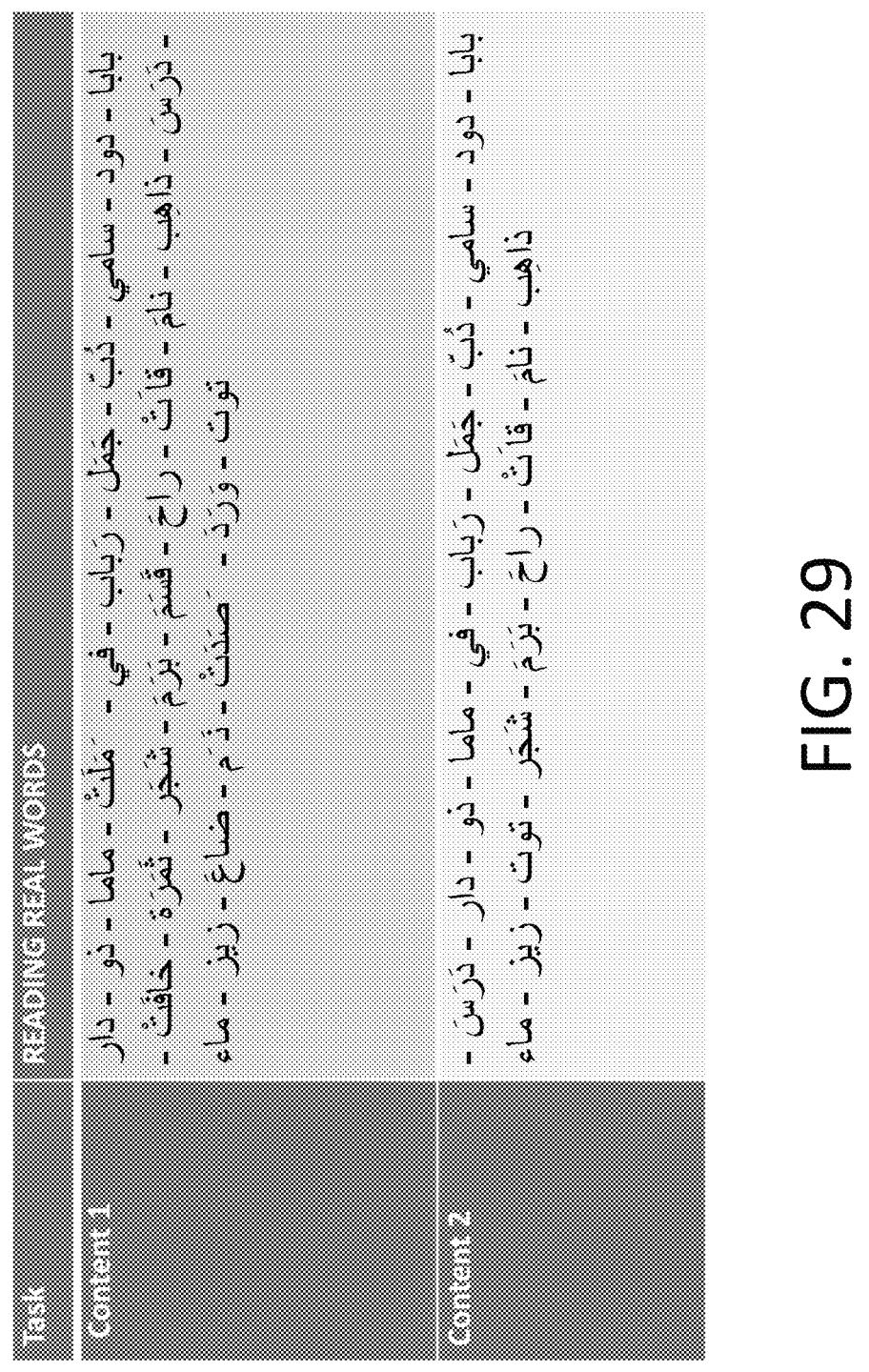
Figure 31:
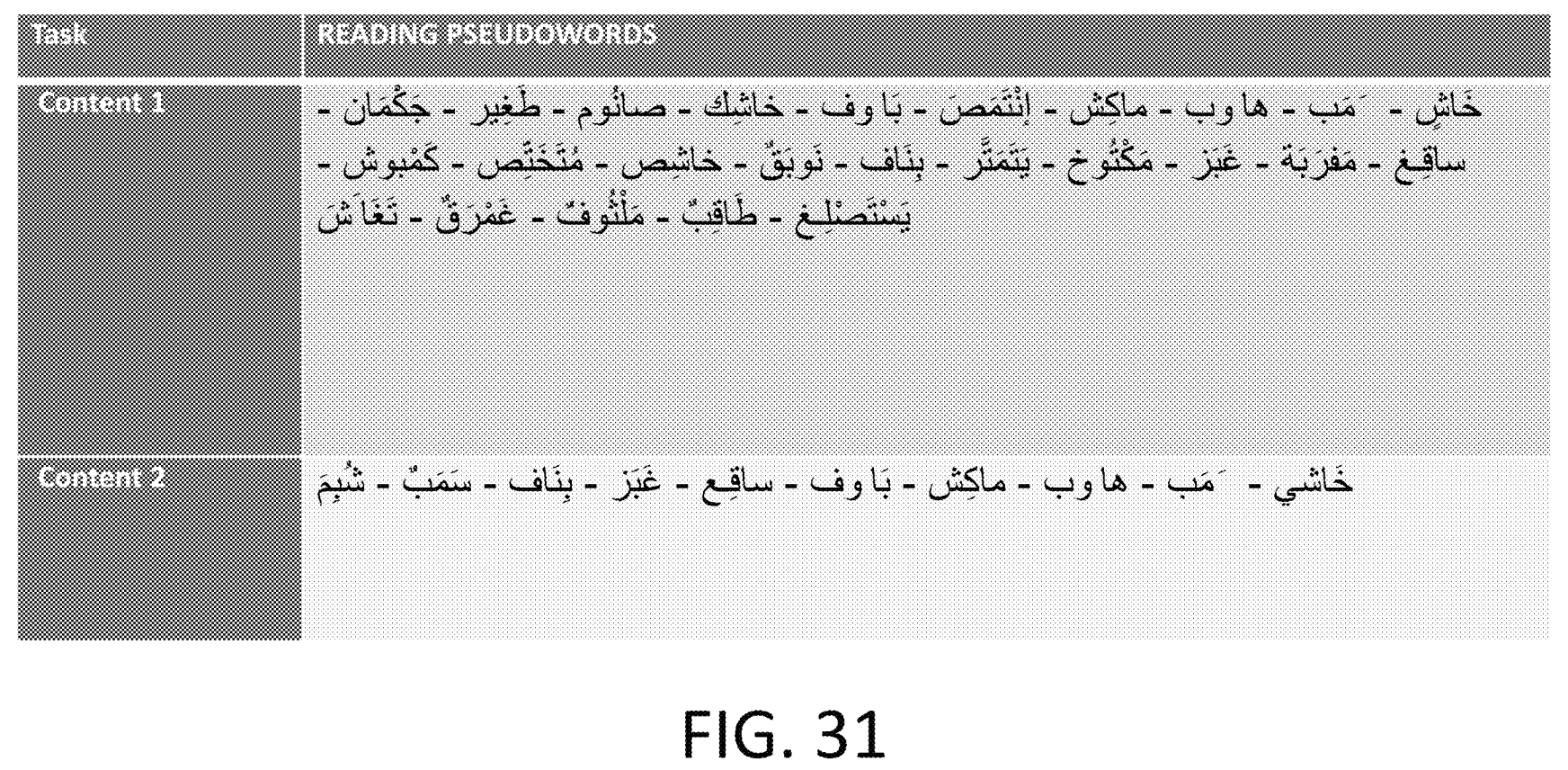
Figure 32:
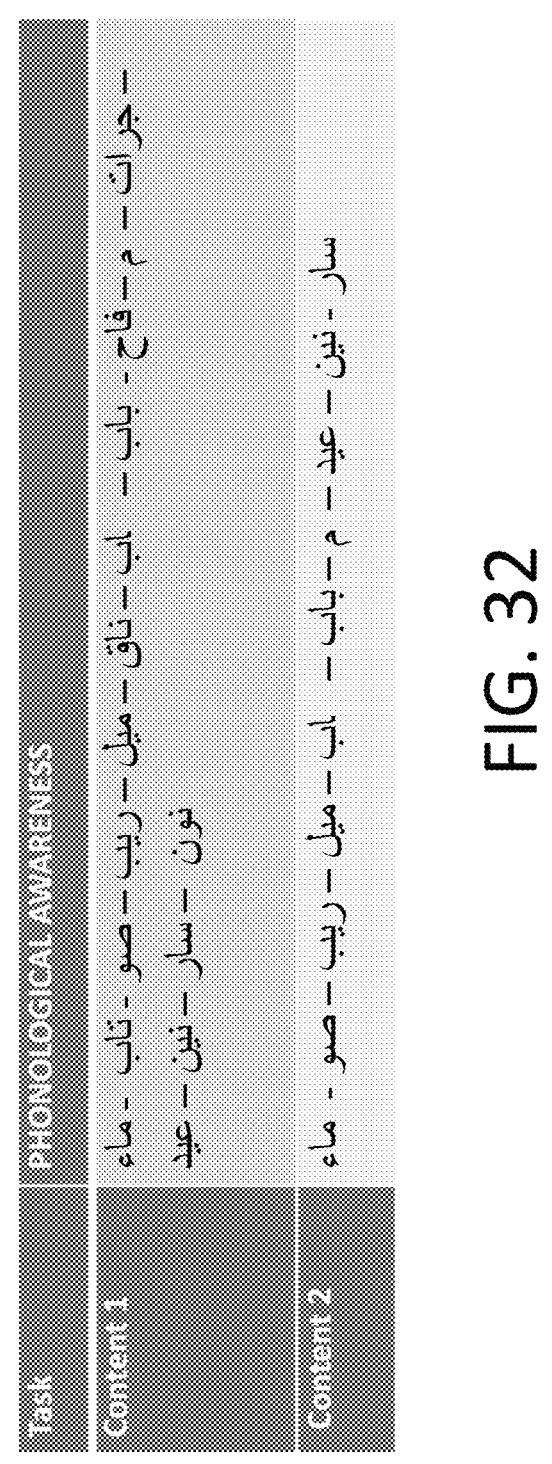
Figure 33:
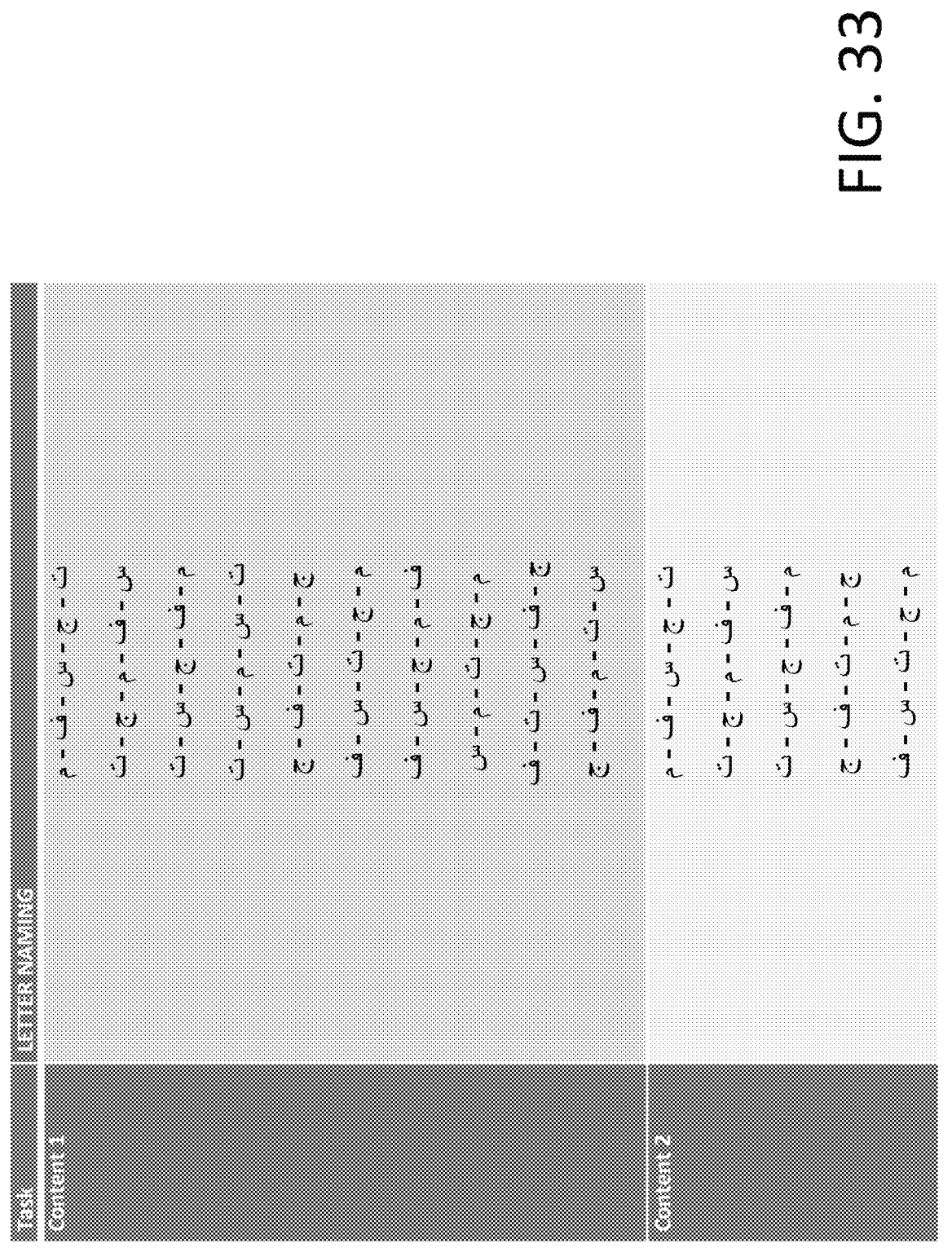

FIGS. 27 to 35 are example tables that show example words, numbers, or syllables, and sentences that are used for a particular task. For example, as shown in FIG. 31, a table is shown that is number of items for "Reading Pseudo-words," there are 25 words in Content 1 and 10 words in Content 2.

In embodiments, the number of words determined in Content 2 is different from the number of words determined in Content 1. In embodiments, the difference of the number of words in Content 2 from Content 1 is based on assessments that were completed in different countries and schools having students from grade 1 to 6. In embodiments, the set timespans and number of questions were tracked for all tasks versus actual completed question count and time per task. Thus, it was determined which tasks needed an increase in timespan or reducing the number of questions in order to keep all benchmarks based on tasks to current users (e.g., students).

FIG. 36 is an example table that shows the number of questions asked for a particular type of task. For example, for "Phonological Awareness," there are 15 in Question Count 1 and 10 in Question Count 2.

Figure 37:
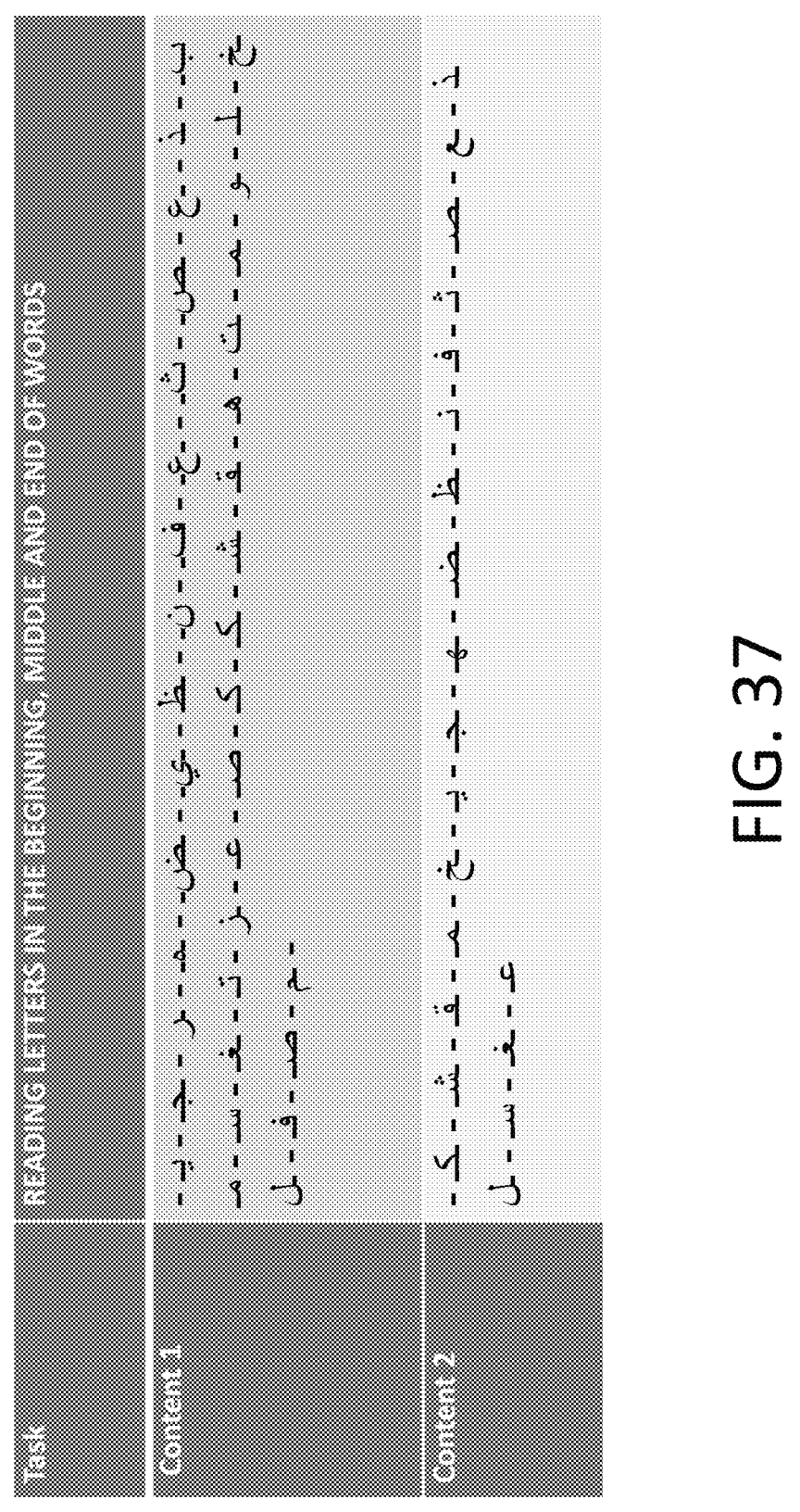
Figure 38:
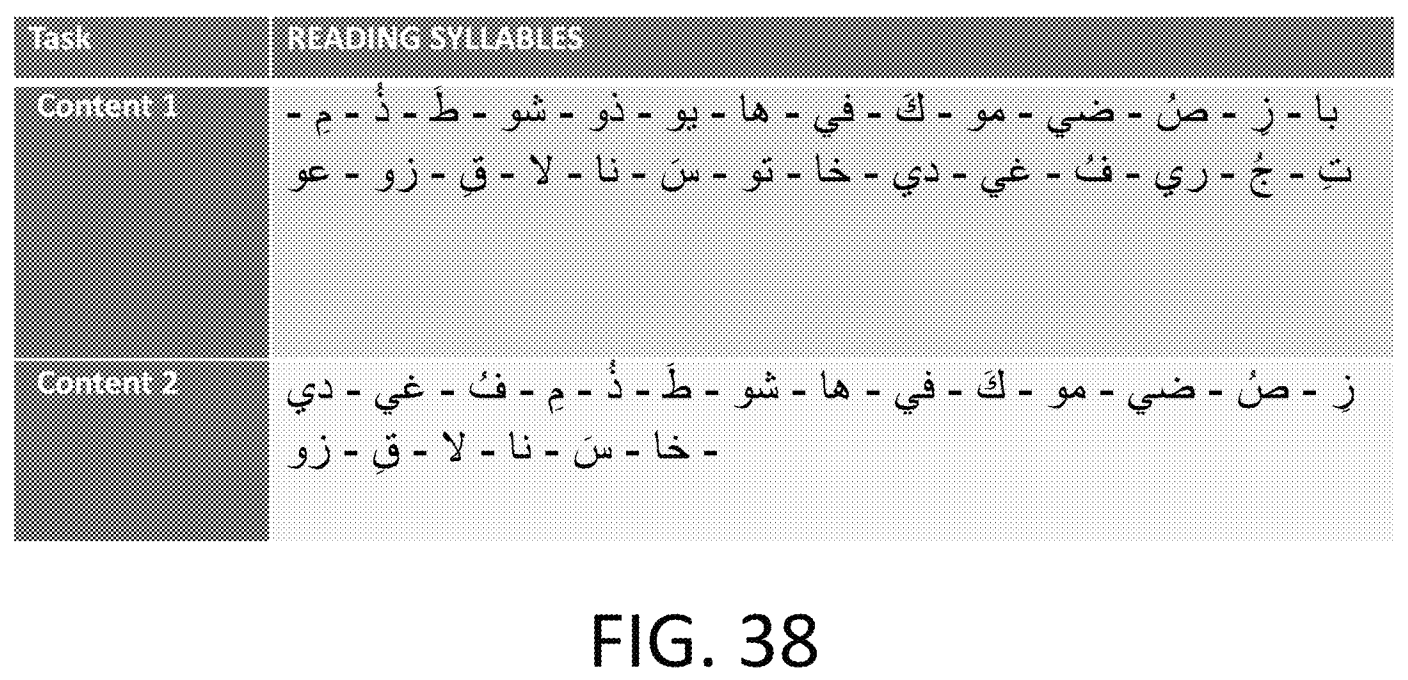
Figure 41:
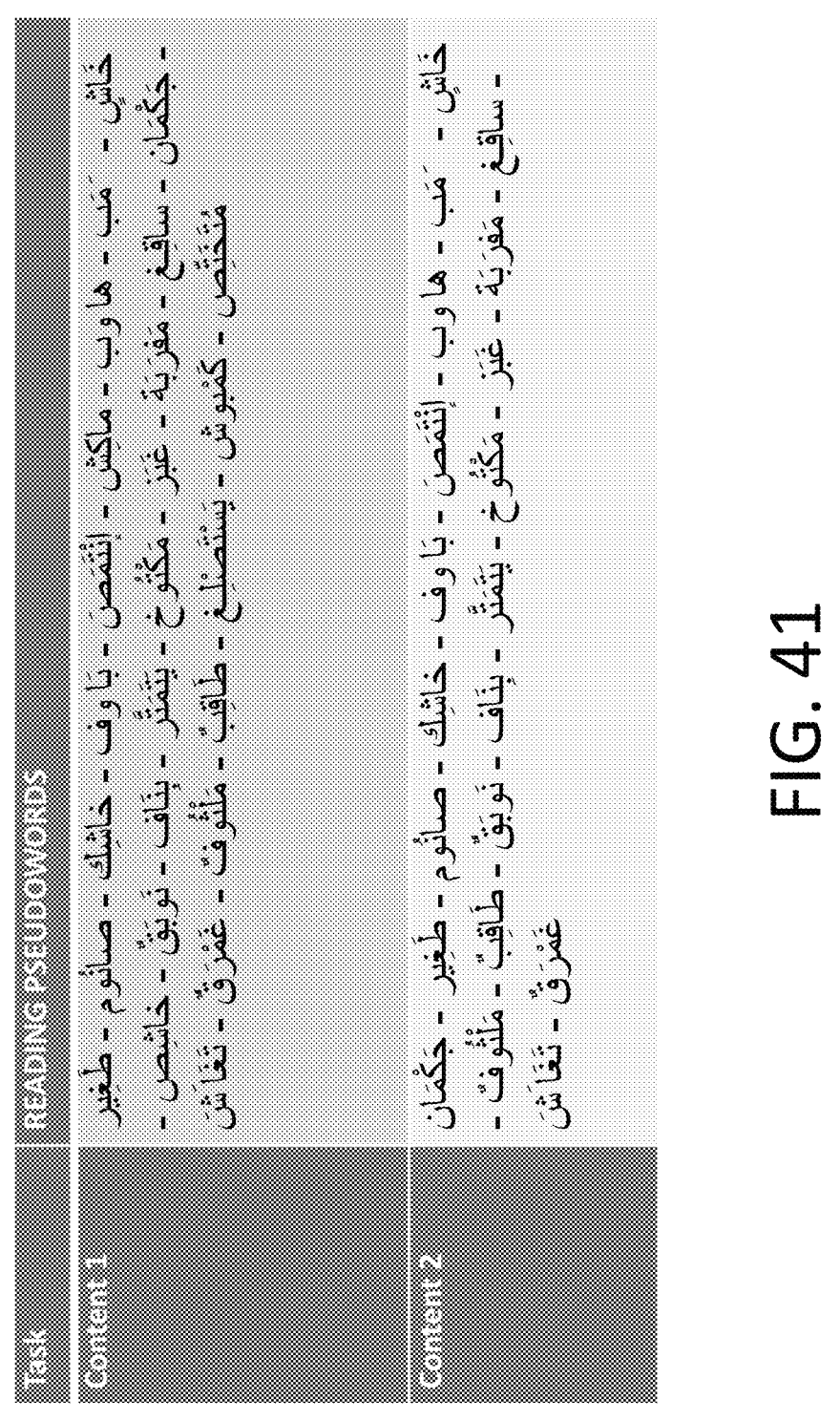
Figure 42:
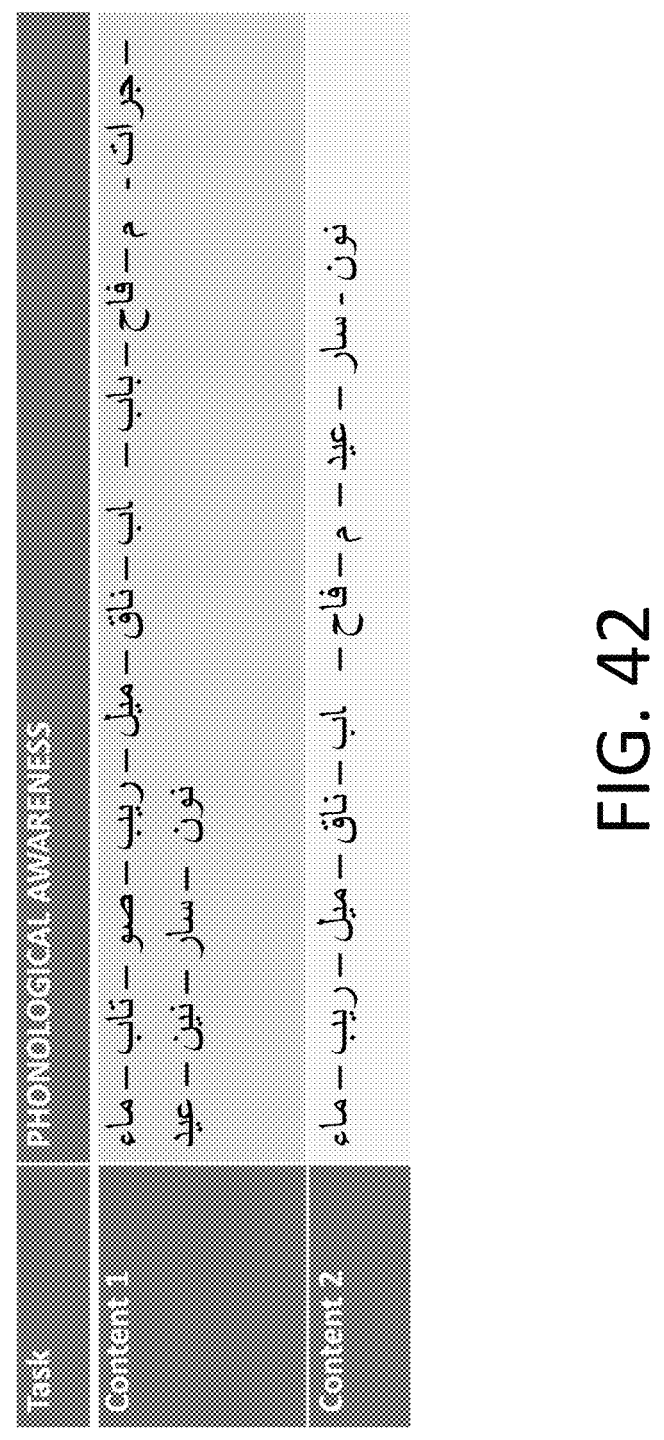
Figure 43:
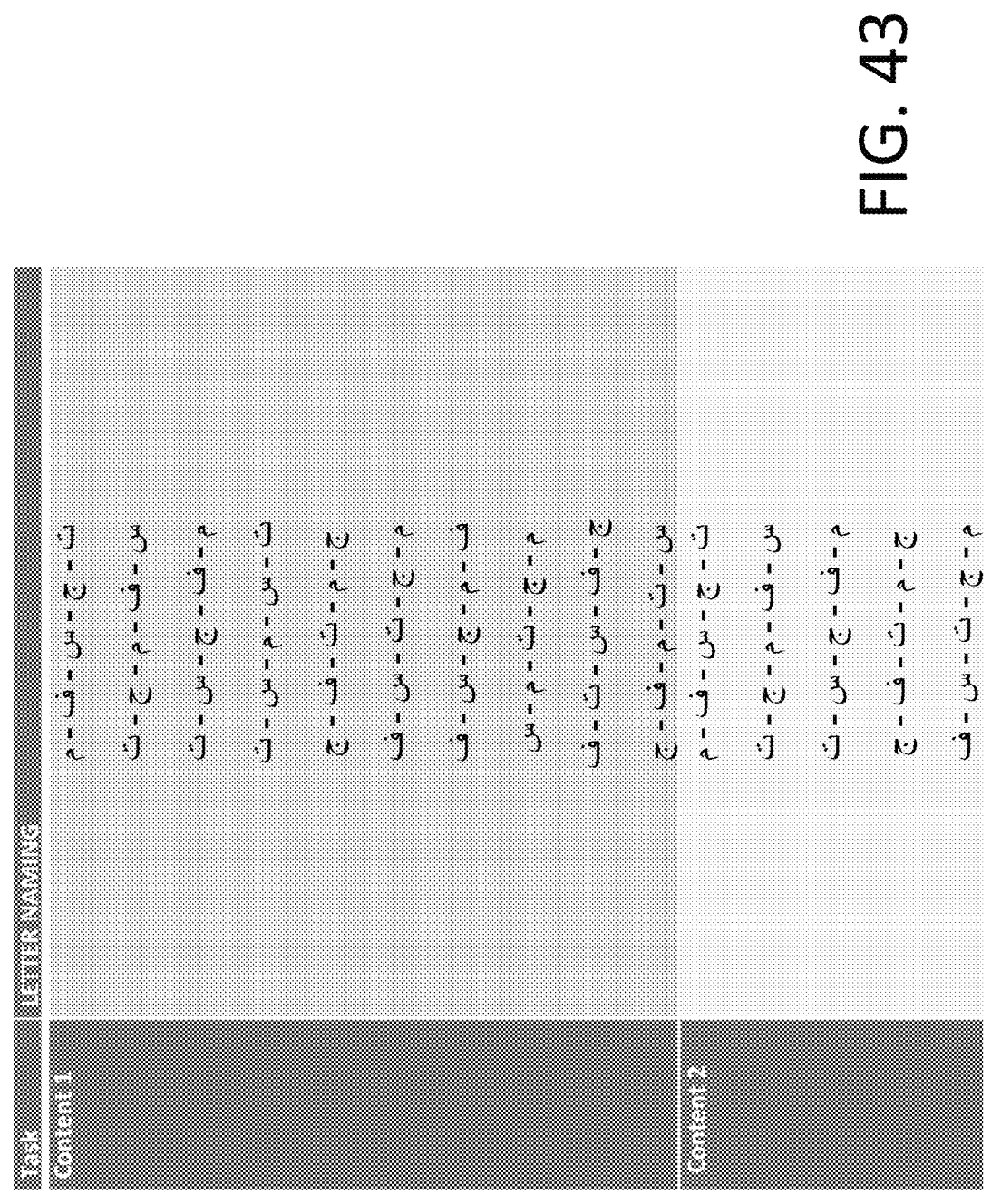
Figure 45:
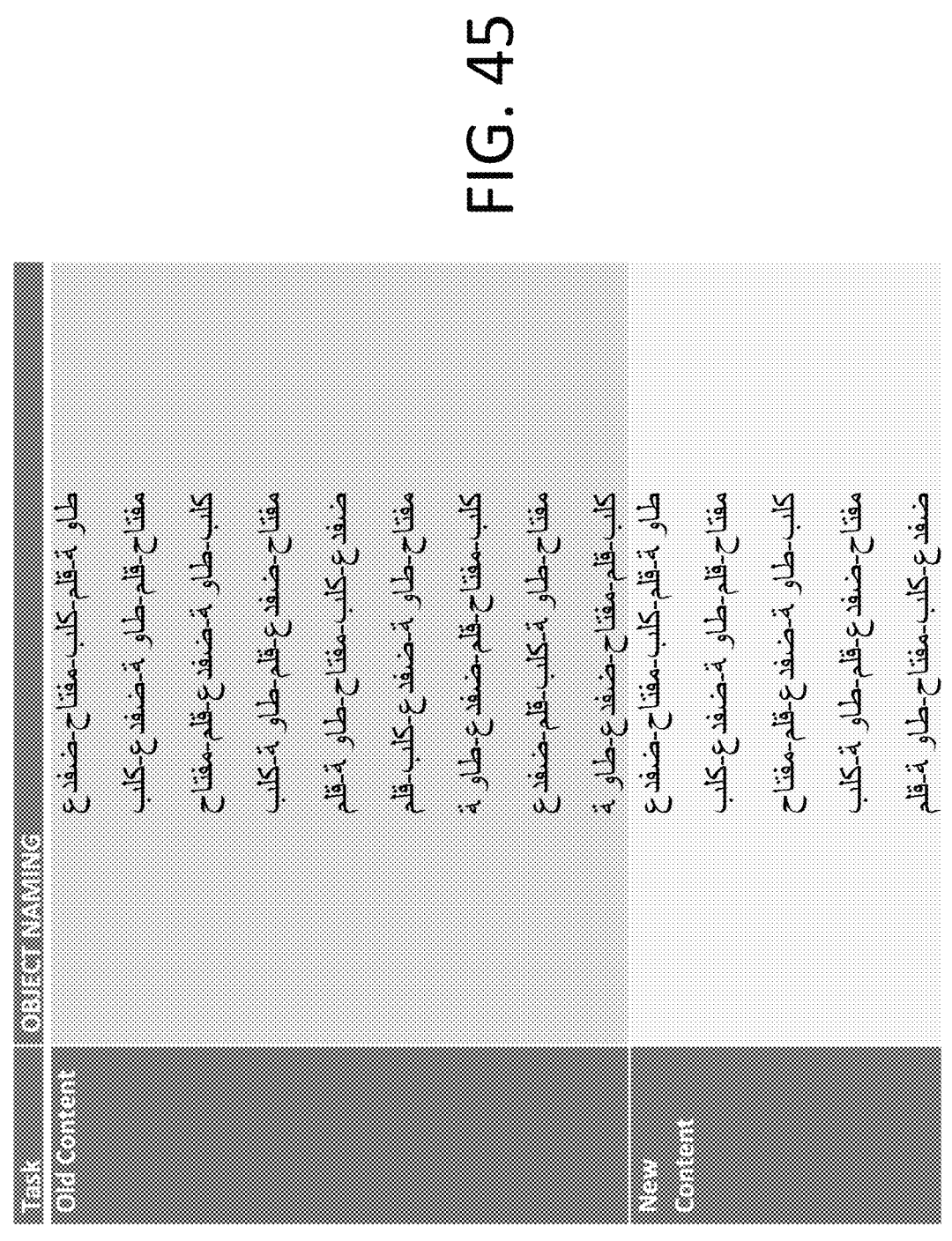

FIGS. 37 to 46 are additional example tables that provide examples of different types of words, sentences, numbers, etc., that are different questions for different types of tasks. In embodiments, the contents are the questions. Each task has a content which contain list of words, characters or pseudo words separated by dashes. Thus, each word, character or pseudo word represent a question. For example: أ – ب – ت (which are Arabic symbols) means the task has three questions and the student will see each question alone in the same order similar to a sliding slider. أ then ب then ت

FIG. 47 is an example table that shows an amount of time associated with a particular type of task. For example, for "Object Naming," has 5 seconds for Timespan 1 and 10 seconds for Timespan 2. As shown in FIG. 47, the value in Timespan 2 is greater than the value in Timespan 1. In embodiments, timespan is a predefined time (in seconds) per question per task. Thus, a user (e.g., a student) is given this timespan to see and answer each question per task, after that, a new question will be displayed regardless if the student answered the question or not. For example, Task A has 20 questions and a timespan of 2 seconds. The student will see one question a time for 2 seconds each until the 20 questions are completed.

FIG. 49 is an example graphical display that shows results for a particular student. In embodiments, the example graphical display is generated after a user of the learning system (e.g., learning system 100) performs the tasks as shown in the graphical display. For example, as shown in FIG. 49, a user of the learning system may obtain a score of 7.4 for the task of "Reading Text." As shown in FIG. 49, the Z-score will be 0.7 and the percentile of the user (in comparison to other users of the learning system) is shown to be 67%. While particular scores, Z-scores, and percentiles are shown, these are non-limiting examples, and the particular scores may correspond to different Z-scores and percentiles.

Figure 51:
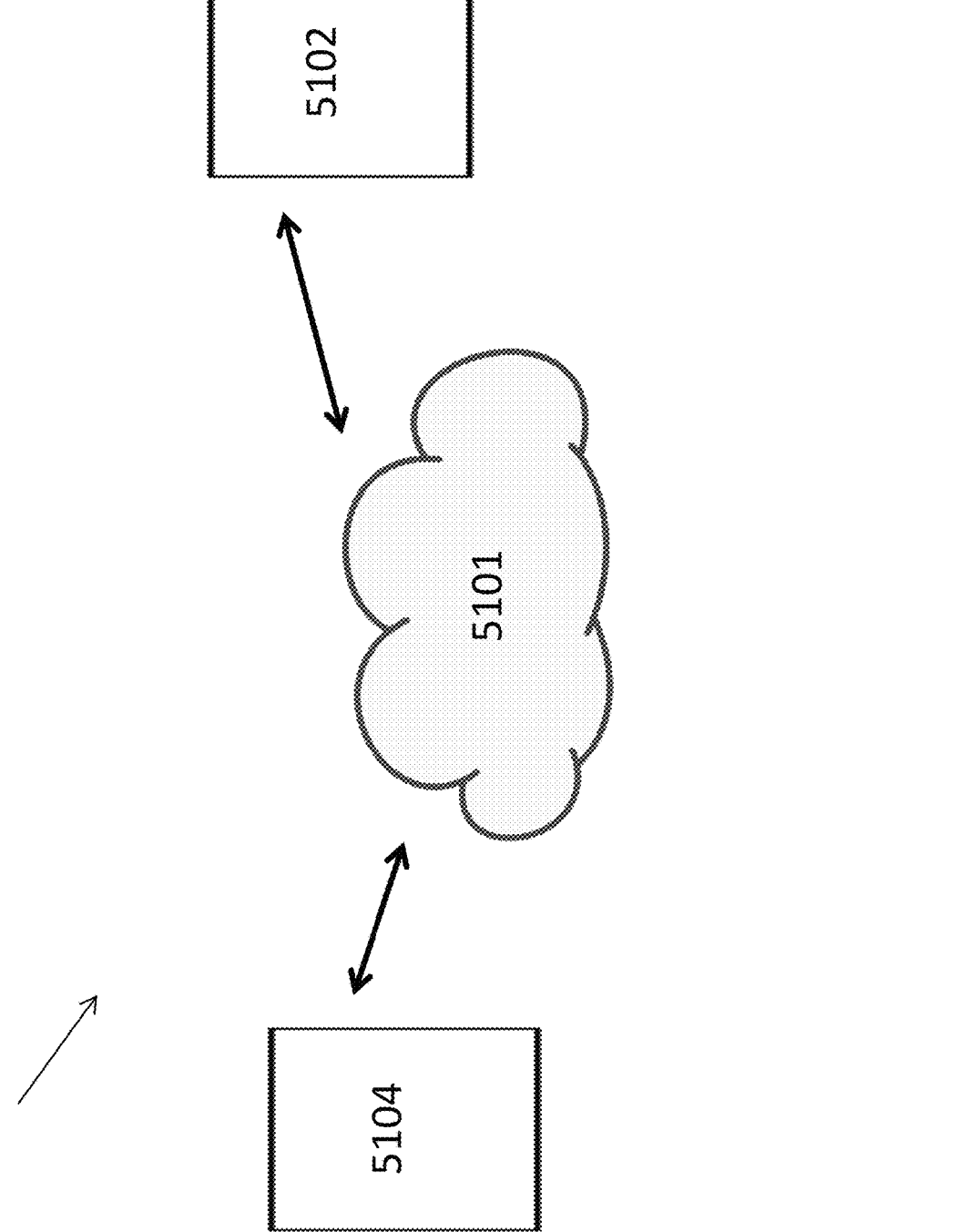
FIG. 51 is a diagram of an example networking environment.

FIG. 50 is an example graphical display that shows how different assessments and benchmarks are used to evaluate a user's learning skills when using the learning system. As shown in FIG. 50, the graphical display explains to someone who may evaluate the user (e.g., the student using learning system 100) what assessment results are and how they are displayed, bar charts for benchmarks and also assessment scales. FIG. 51 is a diagram of example environment 5100 in which systems, devices, and/or methods described herein may be implemented. FIG. 51 shows network 5101, device 5102 and learning system 5104.

Network 5101 may include a local area network (LAN), wide area network (WAN), a metropolitan network (MAN), a telephone network (e.g., the Public Switched Telephone Network (PSTN)), a Wireless Local Area Networking (WLAN), a WiFi, a hotspot, a Light fidelity (LiFi), a Worldwide Interoperability for Microware Access (WiMax), an ad hoc network, an intranet, the Internet, a satellite network, a GPS network, a fiber optic-based network, and/or combination of these or other types of networks. Additionally, or alternatively, network 500 may include a cellular network, a public land mobile network (PLMN), a second generation (2G) network, a third generation (3G) network, a fourth generation (4G) network, a fifth generation (5G) network, and/or another network.

In embodiments, network 5101 may allow for devices describe any of the described figures to electronically communicate (e.g., using emails, electronic signals, URL links, web links, electronic bits, fiber optic signals, wireless signals, wired signals, etc.) with each other so as to send and receive various types of electronic communications.

Device 5102 may include any computation or communications device that is capable of communicating with a network (e.g., network 701). For example, user device 5102 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a smart phone, a desktop computer, a laptop computer, a tablet computer, a camera, a personal gaming system, a television, a set top box, a digital video recorder (DVR), a digital audio recorder (DUR), a digital watch, a digital glass, or another type of computation or communications device.

User device 5102 may receive and/or display content. The content may include objects, data, images, audio, video, text, files, and/or links to files accessible via one or more networks. Content may include a media stream, which may refer to a stream of content that includes video content (e.g., a video stream), audio content (e.g., an audio stream), and/or textual content (e.g., a textual stream). In embodiments, an electronic application may use an electronic graphical user interface to display content and/or information via user device 5102. User device 5102 may have a touch screen and/or a keyboard that allows a user to electronically interact with an electronic application. In embodiments, a user may swipe, press, or touch user device 5102 in such a manner that one or more electronic actions will be initiated by user device 5102 via an electronic application. User device 5102 may receive electronic information from learning system 5104 and generate and display graphs such as those described in the figures above.

User device 5102 may include a variety of applications, such as, for example, an e-mail application, a telephone application, a camera application, a video application, a multi-media application, a music player application, a visual voice mail application, a contacts application, a data organizer application, a calendar application, an instant messaging application, a texting application, a web browsing application, a blogging application, and/or other types of applications (e.g., a word processing application, a spread-sheet application, etc.).

Figure 52:
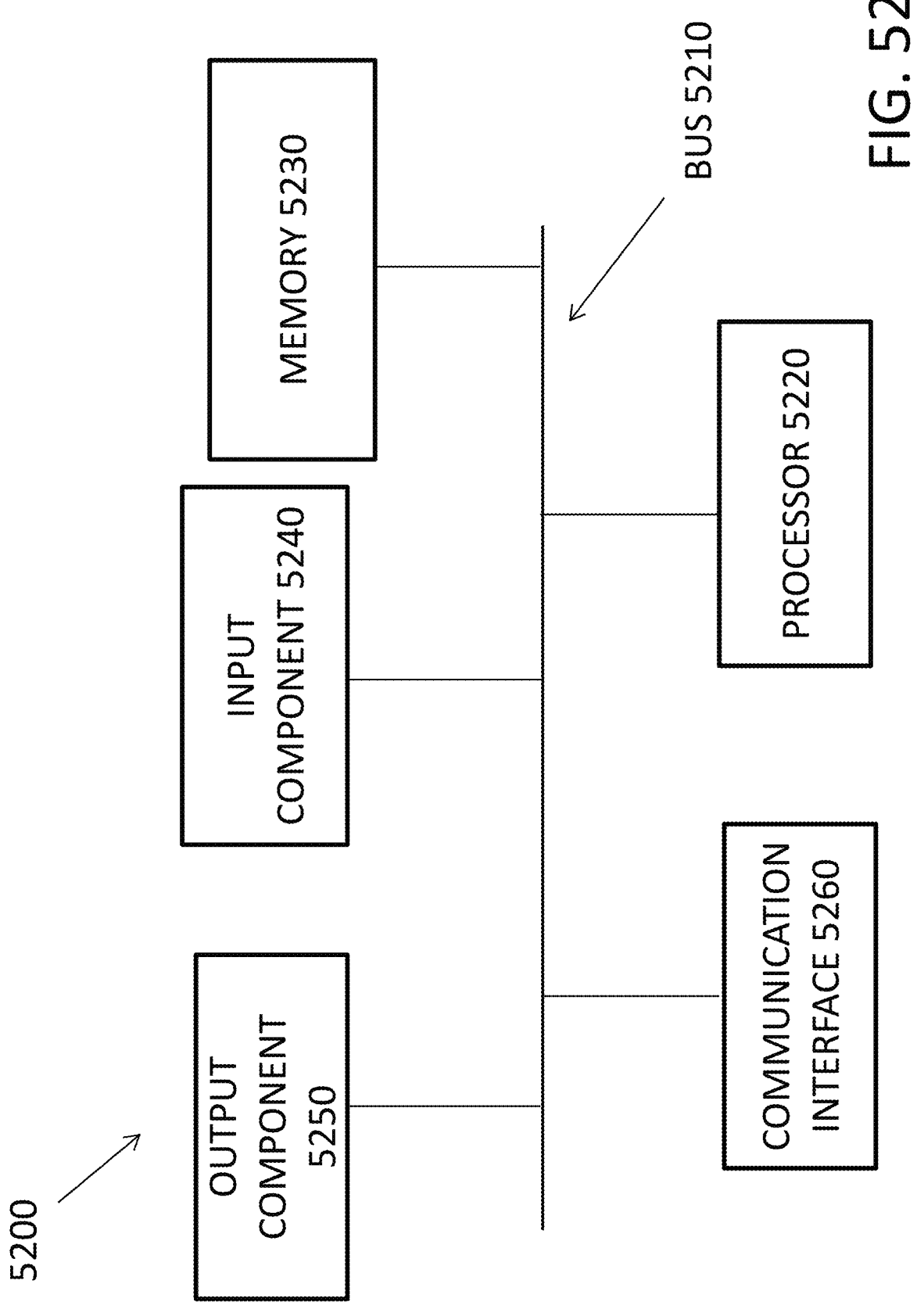
FIG. 52 is a diagram of an example computer.

FIG. 52 is a diagram of example components of a device 5200. Device 5200 may correspond to user device 5102 or learning system 5104. Alternatively, or additionally, user device 5102 and learning system 5104 may include one or more devices 5200 and/or one or more components of device 5200.

As shown in FIG. 52, device 5200 may include a bus 5210, a processor 5220, a memory 5230, an input component 5240, an output component 5250, and a communications interface 5260. In other implementations, device 5200 may contain fewer components, additional components, different components, or differently arranged components than depicted in FIG. 52. Additionally, or alternatively, one or more components of device 5200 may perform one or more tasks described as being performed by one or more other components of device 5200.

Bus 5210 may include a path that permits communications among the components of device 5200. Processor 5220 may include one or more processors, microprocessors, or processing logic (e.g., a field programmable gate array (FPGA) or an application specific integrated circuit (ASIC))

that interprets and executes instructions. Memory 5230 may include any type of dynamic storage device that stores information and instructions, for execution by processor 5220, and/or any type of non-volatile storage device that stores information for use by processor 5220. Input component 5240 may include a mechanism that permits a user to input information to device 5200, such as a keyboard, a keypad, a button, a switch, voice command, etc. Output component 5250 may include a mechanism that outputs information to the user, such as a display, a speaker, one or more light emitting diodes (LEDs), etc.

Communications interface 5260 may include any transceiver-like mechanism that enables device 5200 to communicate with other devices and/or systems. For example, communications interface 5260 may include an Ethernet interface, an optical interface, a coaxial interface, a wireless interface, or the like.

In another implementation, communications interface 5260 may include, for example, a transmitter that may convert baseband signals from processor 5220 to radio frequency (RF) signals and/or a receiver that may convert RF signals to baseband signals. Alternatively, communications interface 5260 may include a transceiver to perform functions of both a transmitter and a receiver of wireless communications (e.g., radio frequency, infrared, visual optics, etc.), wired communications (e.g., conductive wire, twisted pair cable, coaxial cable, transmission line, fiber optic cable, waveguide, etc.), or a combination of wireless and wired communications.

Communications interface 5260 may connect to an antenna assembly (not shown in FIG. 52) for transmission and/or reception of the RF signals. The antenna assembly may include one or more antennas to transmit and/or receive RF signals over the air. The antenna assembly may, for example, receive RF signals from communications interface 5260 and transmit the RF signals over the air, and receive RF signals over the air and provide the RF signals to communications interface 5260. In one implementation, for example, communications interface 5260 may communicate with network 5101.

As will be described in detail below, device 5200 may perform certain operations. Device 5200 may perform these operations in response to processor 5220 executing software instructions (e.g., computer program(s)) contained in a computer-readable medium, such as memory 5230, a secondary storage device (e.g., hard disk, CD-ROM, etc.), or other forms of RAM or ROM. A computer-readable medium may be defined as a non-transitory memory device. A memory device may include space within a single physical memory device or spread across multiple physical memory devices. The software instructions may be read into memory 5230 from another computer-readable medium or from another device. The software instructions contained in memory 5230 may cause processor 5220 to perform processes described herein. Alternatively, hardwired circuitry may be used in place of or in combination with software instructions to implement processes described herein. Thus, implementations described herein are not limited to any specific combination of hardware circuitry and software.

It will be apparent that example aspects, as described above, may be implemented in many different forms of software, firmware, and hardware in the implementations illustrated in the figures. The actual software code or specialized control hardware used to implement these aspects should not be construed as limiting. Thus, the operation and behavior of the aspects were described without reference to the specific software code—it being understood that software and control hardware could be designed to implement the aspects based on the description herein.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

While various actions are described as selecting, displaying, transferring, sending, receiving, generating, notifying, and storing, it will be understood that these example actions are occurring within an electronic computing and/or electronic networking environment and may require one or more computing devices, as described in FIG. 7, to complete such actions.

No element, act, or instruction used in the present application should be construed as critical or essential unless explicitly described as such. Also, as used herein, the article "a" is intended to include one or more items and may be used interchangeably with "one or more." Where only one item is intended, the term "one" or similar language is used. Further, the phrase "based on" is intended to mean "based, at least in part, on" unless explicitly stated otherwise.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. A method, comprising:
receiving, by an electronic communications system, an electronic assessment of a user, wherein the electronic communications system includes memory and a processor;
reducing, by the electronic communications system, noise in audio features of the electronic assessment, wherein the reducing the noise is based on a sample audio spectrogram of the user from previous recordings;
receiving, by the electronic communications system, historical electronic information;
analyzing by the electronic communications system the electronic assessment based on the historical information, wherein the analyzing the electronic assessment includes:
analyzing sound wave slots in a time T, wherein a portion of the sound wave slots with a null frequency,
determining that the portion of the sound wave slots with null frequency do not affect speech classification,
removing the sound wave slots with the null frequency,
segmenting other sound wave slots with frequency into smaller audio clips based on a set timespan, wherein the smaller audio clips result in an equal length input for a particular question asked of the user,
wherein the equal length of each of the smaller audio clips is based on a total number of system generated communications sent to the user within a particular amount of time, normalizing audio volume of the electronic assessment to be the same as other electronic assessments from other users,
padding each of the smaller audio clips, wherein the padding is added to the smaller audio clips' starts and ends,
wherein the padding maintains an equal wave input for each of the smaller audio clips to prevent the smaller audio clips from having different lengths, and
wherein the padding of each of the smaller audio clips does not affect the classification of each of the smaller audio clips,
excluding any of the smaller audio clips that are labeled as including no answer; and
determining, by the electronic system, a learning disability of the user based on the analyzing the historical information and the electronic assessment, wherein the determining the learning disability is based on: a word error rate (WER) and a character error rate (CER); and
receiving, by the electronic communication system, a training set,
labeling the training set as: no answer, wrong, partially correct, or correct,
conducting, by the electronic communication system, training of the electronic communication system, wherein the training includes running a Long Short-Term Memory (LSTM) algorithm and a convolutional neural network (CNN) algorithm,
wherein the LTSM algorithm is configured to apply a reading text task to maintain the dependencies between words as a sentence and overcome corrections by other user;
classifying electronic inputs from sampled student recorded answers in order to be classified into letters and converting to text to be compared with the question text and result in one of the following categories: correct, partially correct, or wrong;
combining the CNN algorithm results and the LSTM algorithm results; and
validating the combination of the outputs of the CNN algorithm and the LSTM algorithm, wherein the validating is used to determine the word error rate (WER) and the character error rate (CER).

2. The method of claim 1, wherein the historical information includes time information.

3. The method of claim 2, wherein the electronic assessment includes additional time information.

4. The method of claim 3, wherein the determining the learning disability is based on comparing the time information to the additional time information.

5. The method of claim 1, wherein the electronic assessment includes an electronic display of a first reading assessment.

6. The method of claim 5, wherein the electronic assessment includes another electronic display of a second reading assessment.

7. The method of claim 6, wherein the electronic learning system determines the learning disability based on determining an error made by the user in the first reading assessment but without any error made by the user in the second reading assessment.

8. A device, comprising:
memory, and
a processor, coupled to the memory, the processor to:
receive an electronic assessment of a user; receive historical electronic information;

analyze the electronic assessment based on the historical information, wherein the analyzing the electronic assessment includes the processor to:

analyze sound wave slots in a time T, wherein a portion of the sound wave slots with a null frequency, determine that the portion of the sound wave slots with null frequency do not affects peech classification, remove the sound wave slots with the null frequency, segment other sound wave slots with frequency into smaller audio clips based on a set timespan, wherein the smaller audio clips result in an equal length input for a particular question asked of the user, wherein the equal length of each of the smaller audio clips is based on a total number of system generated communications sent to the user within a particular amount of time, normalize audio volume of the electronic assessment to be the same as other electronic assessments from other users, pad each of the smaller audio clips, wherein the padding is added to the smaller audio clips' starts and ends, wherein the padding maintains an equal wave input for each of the smaller audio clips to prevent the smaller audio clips from having different lengths, and wherein the padding of each of the smaller audio clips does not affect the classification of each of the smaller audio clips, exclude any of the smaller audio clips that are labeled as including no answer; and determine a learning disability of the user based on the analyzing the historical information and the electronic assessment, wherein the determining the learning disability is based on: a word error rate (WER) and a character error rate (CER); and receiving, by the electronic communication system, a training set, labeling the training set as: no answer, wrong, partially correct, or correct, conducting, by the electronic communication system, training of the electronic communication system, wherein the training includes running a Long Short-Term Memory (LSTM) algorithm and a convolutional neural network (CNN) algorithm, wherein the LTSM algorithm is configured to apply a reading text task to maintain the dependencies between words as a sentence and overcome corrections by other user;

classifying electronic inputs from sampled student recorded answers in order to be classified into letters and converting to text to be compared with the question text and result in one of the following categories: correct, partially correct, or wrong;

combining the CNN algorithm results and the LSTM algorithm results; and validating the combination of the outputs of the CNN algorithm and the LSTM algorithm, wherein the validating is used to determine the word error rate (WER) and the character error rate (CER).

9. The device of claim 8, wherein the electronic assessment includes electronic time information.

10. The device of claim 9, wherein the determining the learning disability includes analyzing the electronic time information against the historical electronic information.

11. The method of claim 1, wherein the analyzing, by the electronic communications system, the electronic assessment includes:

analyzing spoken words, wherein the spoken words are converted to electronic form for the electronic communication system to analyze;

analyzing an amount of time that it takes for the spoken words to be spoken and assigning a first score;

determining if the first score is less than a first benchmark score;

analyzing if the spoken words are grammatically correct and assigning a second score;

determining if the second score is less then a second benchmark score;

determining that the spoken words pass an overall score only if the first score is less than the first benchmark score and the second score is less than the second benchmark score.

12. The method of claim 1, wherein the analyzing the electronic assessment occurs in real-time and the electronic communication system is configured to receive electronic information from multiple users at the same time.

* * * * *